United States Patent
Takahashi et al.

(10) Patent No.: US 10,888,220 B2
(45) Date of Patent: Jan. 12, 2021

(54) INFORMATION PROCESSING APPARATUS, IMAGE GENERATION METHOD, AND COMPUTER-READABLE MEDIUM, WITH ACQUISITION OF CORRECTION COEFFICIENT BY PERFORMING ARITHMETIC OPERATION ON FIRST AND SECOND PARAMETERS

(71) Applicant: CANON KABUSHIKI KAISHA, Tokyo (JP)

(72) Inventors: Riuma Takahashi, Tokyo (JP); Hiroshi Imamura, Kawasaki (JP); Hiroki Uchida, Tokyo (JP); Marek Rozanski, Torun (PL); Tomasz Dziubak, Torun (PL); Tomasz Bajraszewski, Glogowo (PL)

(73) Assignee: Canon Kabushiki Kaisha, Tokyo (JP)

( * ) Notice: Subject to any disclaimer, the term of this patent is extended or adjusted under 35 U.S.C. 154(b) by 294 days.

(21) Appl. No.: 15/919,673

(22) Filed: Mar. 13, 2018

(65) Prior Publication Data

US 2018/0263485 A1 Sep. 20, 2018

(30) Foreign Application Priority Data

Mar. 17, 2017 (JP) .................................. 2017-052761
Sep. 7, 2017 (JP) .................................. 2017-171831

(51) Int. Cl.
*G06T 7/20* (2017.01)
*A61B 3/10* (2006.01)
(Continued)

(52) U.S. Cl.
CPC .......... *A61B 3/0025* (2013.01); *A61B 3/0033* (2013.01); *A61B 3/0041* (2013.01);
(Continued)

(58) Field of Classification Search
CPC ..... A61B 3/0025; A61B 3/102; A61B 3/1233; A61B 3/1241; A61B 3/0041;
(Continued)

(56) References Cited

U.S. PATENT DOCUMENTS

| 8,939,583 | B2 * | 1/2015 | Borycki | ................. A61B 3/102 351/208 |
| 9,875,559 | B2 | 1/2018 | Uchida | |

(Continued)

FOREIGN PATENT DOCUMENTS

| EP | 2 702 930 A1 | 3/2014 |
| EP | 2 702 930 A1 | 5/2014 |

(Continued)

OTHER PUBLICATIONS

Extended European Search Report dated Jun. 26, 2018, issued in European Patent Application No. 18000260.2.

*Primary Examiner* — Siamak Harandi
(74) *Attorney, Agent, or Firm* — Venable LLP

(57) ABSTRACT

Provided is an information processing apparatus including: a first acquisition unit configured to acquire a plurality of pieces of tomographic data based on measurement light controlled to scan the same position of a fundus; a second acquisition unit configured to acquire a correction coefficient by performing an arithmetic operation on a first approximate parameter obtained by transforming, in a first dimension, a parameter of the tomographic data to be used for calculating a motion contrast, and a second approximate parameter obtained by transforming the parameter in a second dimension smaller than the first dimension; a correction unit configured to correct a parameter of at least one piece of tomographic data through use of the correction coefficient; and a generation unit configured to generate a motion
(Continued)

contrast image through use of the at least one piece of tomographic data corrected by the correction unit.

37 Claims, 14 Drawing Sheets

(51) Int. Cl.
*A61B 3/00* (2006.01)
*A61B 3/12* (2006.01)
*G06T 7/00* (2017.01)

(52) U.S. Cl.
CPC ............ *A61B 3/102* (2013.01); *A61B 3/1233* (2013.01); *A61B 3/1241* (2013.01); *G06T 7/0012* (2013.01); *G06T 7/20* (2013.01); *G06T 2207/10101* (2013.01); *G06T 2207/30041* (2013.01)

(58) Field of Classification Search
CPC ....... A61B 3/0033; G06T 7/0012; G06T 7/20; G06T 2207/10101; G06T 2207/30041
See application file for complete search history.

(56) References Cited

U.S. PATENT DOCUMENTS

| | | |
|---|---|---|
| 9,933,246 B2 | 4/2018 | Takeno et al. |
| 2015/0168127 A1 | 6/2015 | Takeno et al. |
| 2015/0374227 A1 | 12/2015 | Takeno et al. |
| 2016/0227999 A1 | 8/2016 | An et al. |
| 2016/0317016 A1 | 11/2016 | Oishi |
| 2016/0317018 A1* | 11/2016 | Sakagawa ............ A61B 3/1233 |
| 2017/0069105 A1 | 3/2017 | Kano et al. |

FOREIGN PATENT DOCUMENTS

| | | | |
|---|---|---|---|
| EP | 3 087 907 A1 | 2/2016 | |
| EP | 3 087 907 A1 | 11/2016 | |
| JP | 2011-135933 A | 7/2011 | |
| JP | 2015-094339 | * 5/2015 | ........... A61B 3/0025 |
| JP | 2015-131107 A | 7/2015 | |
| JP | 2017-046975 A | 3/2017 | |

* cited by examiner

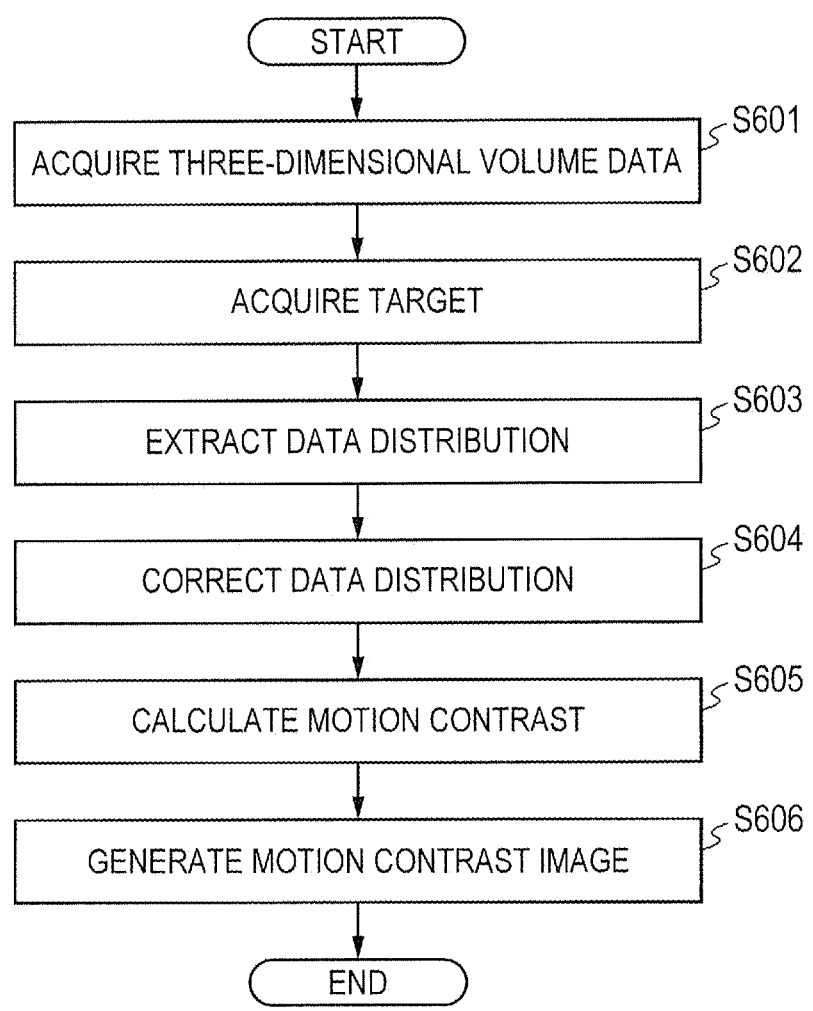

INFORMATION PROCESSING APPARATUS, IMAGE GENERATION METHOD, AND COMPUTER-READABLE MEDIUM, WITH ACQUISITION OF CORRECTION COEFFICIENT BY PERFORMING ARITHMETIC OPERATION ON FIRST AND SECOND PARAMETERS

BACKGROUND

Field

This disclosure relates to an information processing apparatus, an image generation method, and a computer-readable medium.

Description of the Related Art

There is widely used, particularly in the field of ophthalmology, an apparatus (hereinafter referred to as "OCT apparatus") that uses optical coherence tomography capable of acquiring a tomographic image of a measurement target in a non-invasive manner.

In recent years, there has been proposed angiography that uses OCT (OCT angiography: OCTA) as the angiography that does not use a contrast medium. In OCTA, three-dimensional motion contrast data acquired by OCT is projected onto a two-dimensional plane, to thereby generate a blood vessel image (hereinafter referred to as "OCTA image"). In this case, the motion contrast data is data that is obtained by imaging the same cross section of a measurement target repeatedly and detecting a temporal change in the measurement target between the imaged images. The motion contrast data is obtained by calculating a temporal change in phase, vector, or magnitude of complex OCT signals from, for example, a difference, ratio, or correlation between those complex OCT signals.

The motion contrast data also represents a noise portion of an OCT signal as a temporal change in the measurement target. To address this issue, a threshold can be set to remove noises, to thereby acquire a satisfactory OCTA image.

In Japanese Patent Application Laid-Open No. 2015-131107, there is disclosed other methods relating to noise removal from an OCTA image. In the technology disclosed in Japanese Patent Application Laid-Open No. 2015-131107, phase difference information and vector difference information on an OCT signal are multiplied by each other, that is, a calculation result of one type of information is weighted based on a calculation result of another type of information, to thereby generate the motion contrast data. As a result, an OCTA image with a small noise is generated with this technology.

Meanwhile, imaging by OCT causes a change in signal strength of an acquired interference signal depending on, for example, a change in imaging condition. An example of the imaging condition is movement of a measurement target in a depth direction. As a result, deviation of a pixel value may occur in the tomographic image generated based on the interference signal depending on the imaging condition.

In contrast, in Japanese Patent Application Laid-Open No. 2011-135933, there is disclosed a technology of correcting a signal strength by preparing a table for correcting a change in signal strength due to a difference in sensitivity in a depth direction of OCT and preparing a table for correcting deviation of a position in the depth direction of OCT.

However, deviation of the pixel value in the tomographic image, namely, contrast in brightness of the tomographic image, is not only due to movement of a measurement target in the depth direction, but also due to a change in other imaging conditions.

When the tomographic image generated by OCT produces contrast due to deviation of the pixel value, the motion contrast data that is based on the tomographic image is also affected. As a result, the OCTA image, which is a motion contrast image that is based on the motion contrast data, also produces partial contrast.

When the OCTA image produces partial contrast, blood vessels in a dark portion may not be clear. Further, when there is unevenness in representation of blood vessels, a blood vessel density to be measured using OCTA also incurs unevenness at the time of measurement of the blood vessel density. As a result, the blood vessel density cannot be measured accurately using the OCTA image in such cases.

SUMMARY

This disclosure provides an information processing apparatus, an image generation method, and a computer-readable medium, which enable generation of a motion contrast image that suppresses occurrence of contrast due to deviation of tomographic data.

According to one embodiment of this disclosure, there is provided an information processing apparatus including: a first acquisition unit configured to acquire a plurality of pieces of tomographic data each representing information on a cross section of a fundus, which is acquired based on measurement light controlled to scan the same position of the fundus; a second acquisition unit configured to acquire a correction coefficient by performing an arithmetic operation on a first approximate parameter, which is obtained by transforming, in a first dimension, a parameter of a piece of tomographic data to be used for calculating a motion contrast, and a second approximate parameter, which is obtained by transforming the parameter of the piece of tomographic data in a second dimension smaller than the first dimension; a correction unit configured to correct a parameter of at least one piece of tomographic data among the plurality of pieces of tomographic data through use of the correction coefficient; and a generation unit configured to generate a motion contrast image based on a motion contrast calculated through use of the plurality of pieces of tomographic data including the at least one piece of tomographic data corrected by the correction unit.

According to another embodiment of this disclosure, there is provided an information processing apparatus including: a first acquisition unit configured to acquire a plurality of pieces of tomographic data each representing information on a cross section of a fundus, which is acquired based on measurement light controlled to scan the same position of the fundus; a second acquisition unit configured to acquire a correction coefficient by performing an arithmetic operation on a first approximate parameter, which is obtained by transforming, in a first dimension, a parameter of a piece of tomographic data to be used for calculating a motion contrast, and a second approximate parameter, which is obtained by transforming the parameter of the piece of tomographic data in a second dimension smaller than the first dimension; a correction unit configured to correct a threshold of threshold processing to be applied to the parameter of the plurality of pieces of tomographic data through use of the correction coefficient; and a generation unit configured to generate a motion contrast image based on a motion contrast calculated through use of a parameter of at least one piece of tomographic data among the plurality of pieces of tomographic data, which has been subjected to the threshold processing through use of the corrected threshold.

According to another embodiment of this disclosure, there is provided an information processing apparatus including: a first acquisition unit configured to acquire a plurality of pieces of tomographic data each representing information on a cross section of a fundus, which is acquired based on measurement light controlled to scan the same position of the fundus; a second acquisition unit configured to acquire a correction coefficient by performing an arithmetic operation on a first transformed parameter, which is obtained by transforming a parameter of a piece of tomographic data to be used for calculating a motion contrast so that a difference in value between parameters adjacent in a first direction and a second direction is decreased, and a second transformed parameter, which is obtained by transforming the parameter of the piece of tomographic data so that a difference in value between parameters adjacent in the first direction is decreased; a correction unit configured to correct a parameter of at least one piece of tomographic data among the plurality of pieces of tomographic data through use of the correction coefficient; and a generation unit configured to generate a motion contrast image based on a motion contrast calculated through use of the plurality of pieces of tomographic data including the at least one piece of tomographic data corrected by the correction unit.

According to yet another embodiment of this disclosure, there is provided an information processing apparatus including: a first acquisition unit configured to acquire a plurality of pieces of tomographic data each representing information on a cross section of a fundus, which is acquired based on measurement light controlled to scan the same position of the fundus; a second acquisition unit configured to acquire a target of a distribution of a parameter of a piece of tomographic data to be used for calculating a motion contrast; a correction unit configured to correct a distribution of a parameter of at least one piece of tomographic data among the plurality of pieces of tomographic data so that the distribution becomes closer to the target; and a generation unit configured to generate a motion contrast image based on a motion contrast calculated through use of the plurality of pieces of tomographic data including the at least one piece of tomographic data corrected by the correction unit.

According to another embodiment of this disclosure, there is provided an image generation method including: acquiring a plurality of pieces of tomographic data each representing information on a cross section of a fundus, which is acquired based on measurement light controlled to scan the same position of the fundus; acquiring a correction coefficient by performing an arithmetic operation on a first approximate parameter, which is obtained by transforming, in a first dimension, a parameter of a piece of tomographic data to be used for calculating a motion contrast, and a second approximate parameter, which is obtained by transforming the parameter of the piece of tomographic data in a second dimension smaller than the first dimension; correcting a parameter of at least one piece of tomographic data among the plurality of pieces of tomographic data through use of the correction coefficient; and generating a motion contrast image based on a motion contrast calculated through use of the plurality of pieces of tomographic data including the corrected at least one piece of tomographic data.

According to another embodiment of this disclosure, there is provided an image generation method including: acquiring a plurality of pieces of tomographic data each representing information on a cross section of a fundus, which is acquired based on measurement light controlled to scan the same position of the fundus; acquiring a correction coefficient by performing an arithmetic operation on a first approximate parameter, which is obtained by transforming, in a first dimension, a parameter of a piece of tomographic data to be used for calculating a motion contrast, and a second approximate parameter, which is obtained by transforming the parameter of the piece of tomographic data in a second dimension smaller than the first dimension; correcting a threshold of threshold processing to be applied to the parameter of the piece of tomographic data through use of the correction coefficient; and generating a motion contrast image based on a motion contrast calculated through use of a parameter of at least one piece of tomographic data among the plurality of pieces of tomographic data, which has been subjected to the threshold processing through use of the corrected threshold.

According to yet another embodiment of this disclosure, there is provided an image generation method including: acquiring a plurality of pieces of tomographic data each representing information on a cross section of a fundus, which is acquired based on measurement light controlled to scan the same position of the fundus; acquiring a target of a distribution of a parameter of a piece of tomographic data to be used for calculating a motion contrast; correcting a distribution of a parameter of at least one piece of tomographic data among the plurality of pieces of tomographic data so that the distribution becomes closer to the target; and generating a motion contrast image based on a motion contrast calculated through use of the plurality of pieces of tomographic data including the corrected at least one piece of tomographic data.

Further features of the present invention will become apparent from the following description of exemplary embodiments with reference to the attached drawings.

BRIEF DESCRIPTION OF THE DRAWINGS

FIG. 6 is an illustration of a flow of OCTA image generation processing in the first embodiment.

DESCRIPTION OF THE EMBODIMENTS

Figure 1:
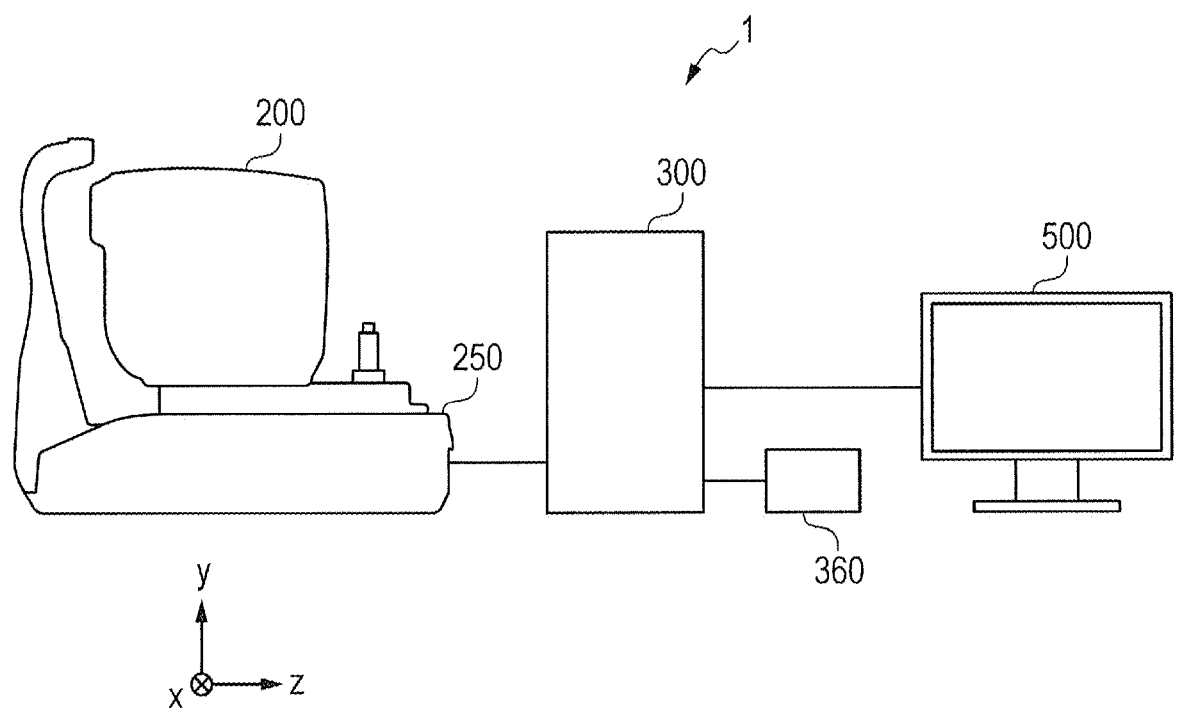
FIG. 1 is a schematic illustration of an entire configuration of an OCT apparatus in a first embodiment of this disclosure.

Preferred embodiments of the present invention will now be described in detail in accordance with the accompanying drawings.

Note that, dimensions, materials, shapes, relative positions of components, and others, which are described in the following embodiments, may be freely selected, and may be changed in accordance with a configuration of an apparatus to which this disclosure is applied or in accordance with various conditions. Further, in the drawings, the same reference symbols are used among the drawings to denote components that are identical or functionally similar to each other. The phrase "same position" herein includes completely the same position and substantially the same position. The phrase "substantially the same position" herein refers to positions that are the same enough to allow generation of a motion contrast image (OCTA image). Further, the phrase "tomographic data" refers to signal data containing information on the cross section of an object to be inspected, as well as data that is based on an interference signal produced by OCT and data obtained by conducting fast Fourier transform (FFT) or any other signal processing on the interference-signal based data.

First Embodiment

Now, with reference to FIG. 1 to FIG. 7C, an OCT apparatus in a first embodiment of this disclosure is described. The OCT apparatus in the first embodiment can suppress occurrence of contrast due to deviation of tomographic data, to thereby generate a satisfactory OCTA image. In the following, the description is given using an eye to be inspected as an example of the object to be inspected.

(Main Unit Configuration)

FIG. 1 is a schematic illustration of an entire configuration of an OCT apparatus 1 in a first embodiment of this disclosure. The OCT apparatus 1 includes an imaging optical system 200, a base 250, a control unit 300, an input unit 360, and a display unit 500.

The imaging optical system (imaging apparatus) 200 is configured to acquire data on an anterior ocular segment, a fundus, and a cross section of the eye to be inspected. The imaging optical system 200 is provided on the base 250, and is held so as to be movable in X, Y, and Z directions relative to the base 250 by, for example, an electromotive stage (not shown).

The control unit (information processing apparatus) 300 is connected to the imaging optical system 200, the input unit 360, and the display unit 500. The control unit 300 is configured to control imaging by the imaging optical system 200, and analyze or reconstruct acquired data on the anterior ocular segment, fundus, and cross section. Further, the control unit 300 is configured to generate, for example, an anterior ocular segment image, a fundus image (scanning laser ophthalmoscope (SLO) image), the tomographic image, and an OCTA image. The control unit 300 can be constructed using a general-purpose computer, but may be constructed as a computer dedicated for the OCT apparatus 1. The input unit 360 is an input device configured to give an instruction to the control unit 300, and is constructed from, for example, a keyboard or a mouse.

The display unit 500 is configured to display, for example, various kinds of information and various images transmitted from the control unit 300 and a mouse cursor that moves in accordance with operation of the input unit 360. The display unit 500 can be constructed using any monitor. In the first embodiment, the imaging optical system 200, the control unit 300, the input unit 360, and the display unit 500 are constructed separately from each other, but a part or all of those components may be constructed in an integrated manner.

(Configurations of Imaging Optical System and Base)

Figure 2:
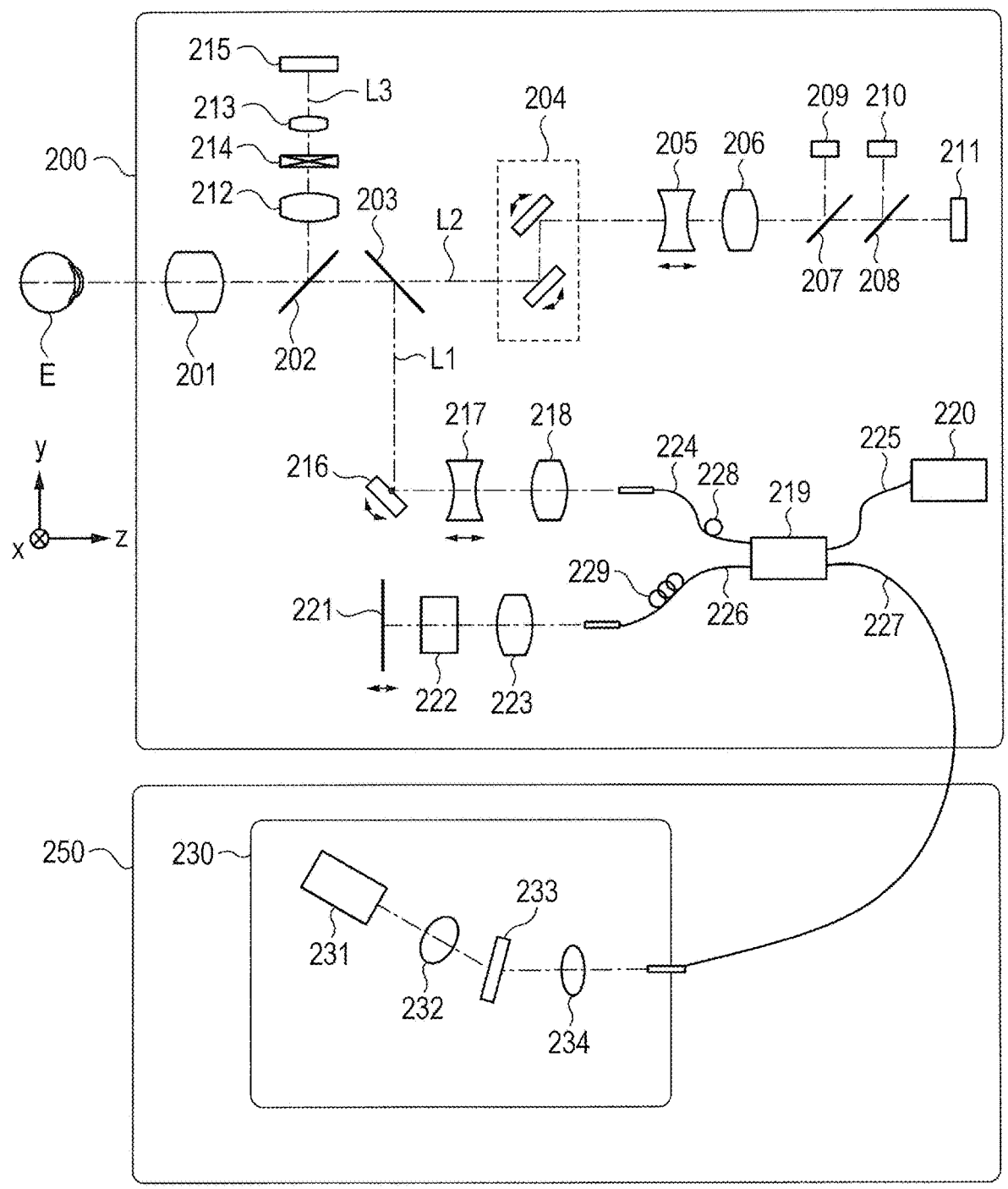
FIG. 2 is a schematic illustration of configurations of an imaging optical system and a base in the first embodiment.

Next, with reference to FIG. 2, configurations of the imaging optical system 200 and the base 250 are described. FIG. 2 is a schematic illustration of the configurations of the imaging optical system 200 and the base 250.

First, an internal configuration of the imaging optical system 200 is described. An objective lens 201 is installed opposite to an eye to be inspected E. A first dichroic mirror 202 and a second dichroic mirror 203 are installed on an optical axis of the objective lens 201. The first and second dichroic mirrors 202 and 203 split the optical path from the objective lens 201 into an optical path L1 of an OCT optical system, an optical path L2 of an SLO optical system used for a fixation lamp, and an optical path L3 for observing the anterior ocular segment based on each wavelength band of light passing through the optical path. In the first embodiment, the optical path L1 of the OCT optical system and the optical path L2 of the SLO optical system for a fixation lamp are arranged in a transmission direction of the first dichroic mirror 202, and the optical path L3 for observing the anterior ocular segment is arranged in a reflection direction of the first dichroic mirror 202. Further, the optical path L2 of the SLO optical system for a fixation lamp is arranged in a transmission direction of the second dichroic mirror 203, and the optical path L1 of the OCT optical system is arranged in a reflection direction of the second dichroic mirror 203. However, arrangement of those optical paths is not limited thereto, and the optical paths may be arranged in an arrangement opposite to the above-mentioned arrangement with respect to the transmission direction and reflection direction of the first dichroic mirror 202 and the second dichroic mirror 203.

The optical path L2 of the SLO optical system for a fixation lamp is used to acquire data on the fundus and to fix the line of sight of the eye to be inspected E. An SLO scanning unit 204, lenses 205 and 206, a mirror 207, a third dichroic mirror 208, a photodiode 209, an SLO optical source 210, and a fixation lamp 211 are installed on the optical path L2. Components other than the fixation lamp 211 on the optical path L2 construct the SLO optical system.

The SLO scanning unit 204 is configured to scan the eye to be inspected E with light emitted from the SLO optical source 210 and the fixation lamp 211. The SLO scanning unit 204 is constructed from an X scanner configured to perform scanning in the X direction and a Y scanner configured to perform scanning in the Y direction. In the first embodiment, the X scanner is constructed from a polygon mirror, and the Y scanner is constructed from a galvano mirror. However, the X scanner and the Y scanner are not limited thereto, and can be constructed using any deflection unit depending on a desired configuration.

The lens 205 is a focus lens, and is driven along an optical path direction indicated by the arrow in FIG. 2 by a motor (not shown) controlled by the control unit 300 for the purpose of focusing of the SLO optical system and the fixation lamp.

The mirror 207 is a prism on which a perforated mirror or a hollow mirror is vapor-deposited, and separates illumination light emitted by the SLO optical source 210 and light emitted by the fixation lamp from return light from the eye to be inspected E. Specifically, the mirror 207 allows passage of illumination light from the SLO optical source 210 and light from the fixation lamp, and reflects return light from the eye to be inspected E to guide the return light toward the photodiode 209. Alternatively, the photodiode 209 may be installed in a passage direction of the mirror 207, and the third dichroic mirror 208, the SLO optical source 210, and the fixation lamp 211 may be installed in a reflection direction of the mirror 207.

The third dichroic mirror 208 splits the optical path L2 into an optical path to the SLO optical source 210 and an optical path to the fixation lamp 211 based on each wavelength band of light passing through the optical path L2. Specifically, the fixation lamp 211 is installed in a transmission direction of the third dichroic mirror 208, and the SLO optical source 210 is installed in a reflection direction of the third dichroic mirror 208. Alternatively, the SLO optical source 210 may be arranged in the transmission direction of the third dichroic mirror 208, and the fixation lamp 211 may be installed in the reflection direction of the third dichroic mirror 208.

The photodiode 209 is configured to detect return light from the eye to be inspected E, and generate a signal corresponding to the return light. The control unit 300 can obtain a front image (SLO image) of the fundus of the eye to be inspected E based on the signal (SLO signal) generated by the photodiode 209.

The SLO optical source 210 generates light having a wavelength of around 780 nm. Light (illumination light) emitted by the SLO optical source 210 is reflected by the third dichroic mirror 208, passes through the mirror 207, and the lenses 206 and 205 in the stated order, and is used for scanning of the eye to be inspected E by the SLO scanning unit 204. The return light from the eye to be inspected E travels back along the same path as that of the illumination light, is reflected by the mirror 207, and then is guided to the photodiode 209. An output signal of the photodiode 209 can be processed by the control unit 300 to obtain a front image of the fundus of the eye to be inspected E.

The fixation lamp 211 can generate visible light to allow a subject to be examined to fix his or her eye. Light emitted by the fixation lamp 211 passes through the third dichroic mirror 208, the mirror 207, and the lenses 206 and 205 in the stated order, and is used for scanning of the eye to be inspected E by the SLO scanning unit 204. At this time, the control unit 300 can cause the fixation lamp 211 to blink in accordance with movement of the SLO scanning unit 204, to thereby form any shape at any position on the eye to be inspected E to allow the subject to be examined to fix his or her eye.

In the first embodiment, the SLO is used as a fundus observation system for observing the fundus, but the configuration of the fundus observation system is not limited thereto. For example, a known observation system, for example, a fundus camera configured to image the fundus, may be used to construct the fundus observation system.

Next, lenses 212 and 213, a split prism 214, and a CCD 215 for observing the anterior ocular segment, which is configured to detect infrared light, are installed on the optical path L3 for observing the anterior ocular segment. Components installed on the optical path L3 for observing the anterior ocular segment construct an anterior ocular segment observation optical system.

On the optical path L3, light having a wavelength of approximately 970 nm is emitted to the anterior ocular segment of the eye to be inspected E from a light source (not shown) for observing the anterior ocular segment. Reflected light from the anterior ocular segment of the eye to be inspected E enters the split prism 214 via the objective lens 201, the first dichroic mirror 202, and the lens 212.

The split prism 214 is arranged at a position conjugate with a pupil of the eye to be inspected E. Light emitted from the split prism 214 enters the CCD 215 via the lens 213.

The CCD 215 has sensitivity at a wavelength of light emitted from the light source (not shown) for observing the anterior ocular segment, specifically, a wavelength of approximately 970 nm. The CCD 215 is configured to detect light reflected by the anterior ocular segment, and generate a signal corresponding to the light reflected by the anterior ocular segment. The control unit 300 can generate an anterior ocular segment image of the eye to be inspected E based on the signal generated by the CCD 215. At this time, the control unit 300 can detect the reflected light that has passed through the split prism 214 with the CCD 215, to thereby detect a distance in the Z direction (depth direction) of the imaging optical system 200 from a split image of the anterior ocular segment to the eye to be inspected E. The generated anterior ocular segment image can be used for, for example, aligning the imaging optical system 200 and the eye to be inspected E.

Next, the optical path L1 of the OCT optical system is described. As described above, the optical path L1 is an optical path for the OCT optical system, and is used to acquire an interference signal for forming a tomographic image of the eye to be inspected E. An XY scanner 216 and lenses 217 and 218 are installed on the optical path L1.

The XY scanner 216 serves as an OCT scanning unit for scanning the eye to be inspected E with measurement light. The XY scanner 216 is illustrated as one mirror, but in actuality, is constructed from two galvano mirrors configured to perform scanning in the X-axis and Y-axis directions, respectively. The configuration of the XY scanner 216 is not limited thereto, and can be constructed using any deflection unit. The XY scanner 216 may be constructed from, for example, a MEMS mirror, which can deflect light in a two-dimensional direction by one mirror.

The lens 217 is a focus lens to be used for focusing measurement light, which is emitted by an optical fiber 224 connected to an optical coupler 219, onto the eye to be inspected E. The lens 217 is driven in an optical-axis direction of the measurement light indicated by the arrow in FIG. 2 by a motor (not shown) controlled by the control unit 300. This focusing causes return light of the measurement light from the eye to be inspected E to be imaged in a spotted manner at the tip of the optical fiber 224 to enter the optical fiber 224. For example, the optical fiber 224, optical members installed on the optical path L1, the first and second dichroic mirrors 202 and 203, and the objective lens 201 construct an OCT measurement optical system for allowing propagation of measurement light in the OCT optical system.

Next, an optical path from an OCT light source 220 and configurations of a reference optical system and a spectroscope 230 are described. The optical fiber 224 is connected to the optical coupler 219. The optical fiber 224 of the OCT measurement optical system, an optical fiber 225 connected to the OCT light source 220, an optical fiber 226 of an OCT reference optical system, and an optical fiber 227 connected to the spectroscope 230 are connected to the optical coupler 219. The optical coupler 219 functions as a splitter configured to split light from the OCT light source 220 into measurement light and reference light, and an interference device configured to cause the return light of the measurement light from the eye to be inspected E and the reference light to interfere with each other to generate interference light. In the first embodiment, the optical fibers 224 to 227 are single-mode optical fibers that are connected to the optical coupler 219 in an integrated manner.

The OCT light source 220 is a super luminescent diode (SLD), which is a representative low-coherent light source. In the first embodiment, the OCT light source 220 having a central wavelength of 855 nm and a wavelength bandwidth of approximately 100 nm is used. The bandwidth is an important parameter because the bandwidth affects a resolution in an optical axis direction of the acquired tomographic image.

While the SLD is used as the OCT light source 220 in the first embodiment, the OCT light source 220 is only required to emit low-coherent light, and for example, an amplified spontaneous emission (ASE) light source may be used as the OCT light source 220. The OCT light source whose central wavelength is a wavelength of near-infrared light can be used in view of the configuration in which the subject to be inspected is an eye. Further, the central wavelength affects a lateral resolution of the acquired tomographic image, and hence a light source whose central wavelength is as short as possible can be used. In the first embodiment, because of both of the reasons, the light source having the central wavelength of 855 nm is used.

Light emitted by the OCT light source 220 passes through the optical fiber 225, and is split into measurement light propagating through the OCT measurement optical system, for example, the optical fiber 224, and reference light propagating through the OCT reference optical system, for example, the optical fiber 226 via the optical coupler 219. The measurement light is radiated to the eye to be inspected E, which is an object to be observed, through a deflection light adjustment device 228 and the optical path L1 of the above-mentioned OCT optical system. Then, the measurement light is reflected or diffused by the eye to be inspected E to reach the optical coupler 219 as return light through the same optical path.

Meanwhile, the reference light travels through the optical fiber 226, a polarization adjustment device 229, a lens 223, and a dispersion compensation glass 222, which is inserted in order to match dispersions of the measurement light and the reference light, and reaches a reference mirror 221 to be reflected by the reference mirror 221. Then, the reference light returns through the same optical path, and reaches the optical coupler 219. The optical fiber 226, the deflection light adjustment device 229, the lens 223, the dispersion compensation glass 222, and the reference mirror 221 construct the OCT reference optical system.

The polarization adjustment device 228 is a polarization adjustment device on the measurement light side, which is arranged on the optical fiber 224, and the polarization adjustment device 229 is a polarization adjustment device on the reference light side, which is arranged on the optical fiber 226. Those polarization adjustment devices 228 and 229 include several looped portions formed by pulling around the respective optical fibers. The polarization adjustment devices 228 and 229 can rotate the looped portions about longitudinal directions of the optical fibers to apply torsion to the fibers, to thereby adjust and match the respective polarization states of the measurement light and the reference light.

The return light of the measurement light from the eye to be inspected E and the reference light are multiplexed by the optical coupler 219 to be interference light. When a state in which the optical path length of the measurement light and the optical path length of the reference light are substantially the same is reached, the return light of the measurement light and the reference light interfere with each other to be interference light. The reference mirror 221 is held so as to be adjustable in the optical-axis direction of the reference light indicated by the arrow in FIG. 2 by a motor or drive mechanism (not shown) controlled by the control unit 300, which enables the optical path length of the reference light to be adjusted to the optical path length of the measurement light that changes depending on a measured part of the eye to be inspected E. The reference light is guided to the spectroscope 230 through the optical fiber 227.

The spectroscope 230 is installed in the base 250. In the spectroscope 230, lenses 232 and 234, a diffraction grating 233, and a line sensor 231 are arranged. The interference light emitted from the optical fiber 227 passes through the lens 234 to become substantially collimated light, and is then dispersed by the diffraction grating 233 and imaged onto the line sensor 231 by the lens 232. The line sensor 231 is given as an example of a light receiving element configured to receive interference light, and output an output signal that depends on the interference light. The control unit 300 can acquire information on a cross section of the eye to be inspected E based on the signal generated by the line sensor 231 to generate a tomographic image.

In the first embodiment, as in the configuration described above, a Michelson interferometer is used as the interferometer, but a Mach-Zehnder interferometer may be used instead. For example, depending on the light amount difference between the measurement light and the reference light, the Mach-Zehnder interferometer can be used when the light amount difference is large, whereas the Michelson interferometer can be used when the light amount difference is relatively small.

With the configuration described above, the OCT apparatus 1 can acquire the tomographic image of the eye to be inspected E, and acquire, for example, an SLO image of the eye to be inspected E, which has high contrast even in the case of infrared light.

(Configuration of Control Unit)

Figure 3:
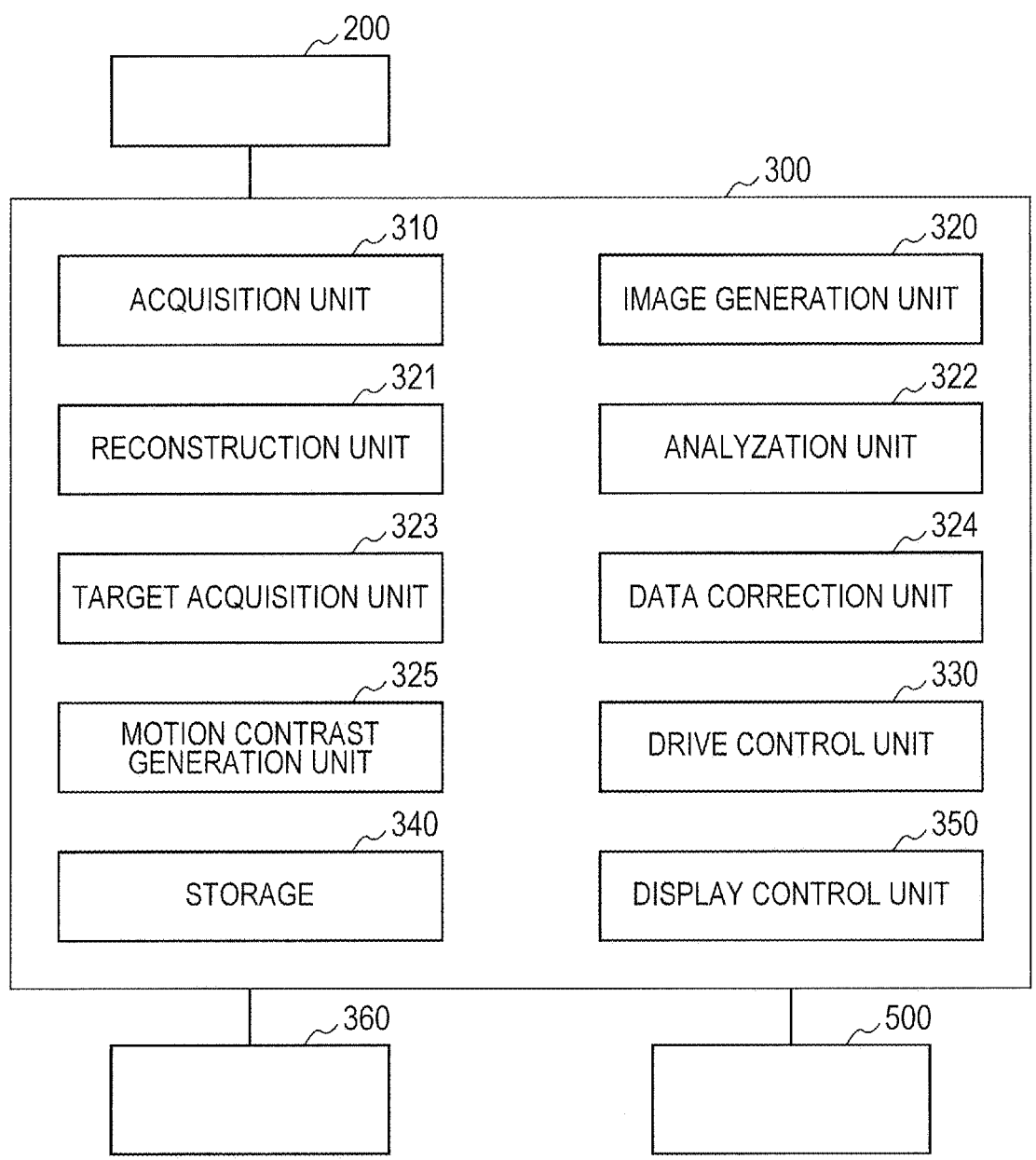
FIG. 3 is a schematic illustration of a configuration of a control unit in the first embodiment.

Now, with reference to FIG. 3, the configuration of the control unit 300 is described. FIG. 3 is a schematic illustration of the configuration of the control unit 300. The control unit 300 includes an acquisition unit 310, an image generation unit 320, a reconstruction unit 321, an analyzation unit 322, a target acquisition unit 323, a data correction unit 324, a motion contrast generation unit 325, a drive control unit 330, a storage 340, and a display control unit 350.

The acquisition unit (first acquisition unit) 310 is configured to acquire various signals from the photodiode 209, the CCD 215, and the line sensor 231 of the imaging optical system 200. Further, the acquisition unit 310 can also acquire, from the image generation unit 320 or the reconstruction unit 321, a Fourier transformed signal generated based on the interference signal from the line sensor 231, a signal obtained by conducting some signal kind of processing on the Fourier transformed signal, or other signals.

The image generation unit (generation unit) 320 is configured to generate an anterior ocular segment image, an SLO image, a tomographic image, and a motion contrast image (OCTA image) based on signals from, for example, the acquisition unit 310, the reconstruction unit 321, and the motion contrast generation unit 325. The image generation unit 320 converts tomographic data of the depth direction (Z direction) at one point in the eye to be inspected E, which is acquired from the acquisition unit 310 or the reconstruction unit 321, into luminance information or density information, to thereby acquire a tomographic image in the depth direction at that point. A scanning method for acquiring an interference signal in the depth direction at one point in the object to be inspected is referred to as "A-scan", and the tomographic image obtained by A-scan is referred to as "A-scan image".

Such A-scan can be performed repeatedly while scanning the object to be inspected in a predetermined traverse direction with measurement light by the XY scanner 216, to thereby acquire a plurality of A-scan images. For example, a tomographic image in the XZ-plane is obtained when the object to be inspected is scanned with measurement light in the X direction by the XY scanner 216, whereas a tomographic image in the YZ-plane is obtained when the object to be inspected is scanned in the Y direction. In this manner, a method of scanning the object to be inspected in a predetermined traverse direction is referred to as "B-scan", and the tomographic image obtained by B-scan is referred to as "B-scan image".

The reconstruction unit 321 is configured to generate three-dimensional volume data of the eye to be inspected E based on an interference signal that is acquired by the acquisition unit 310 from the line sensor 231. With this, imaging data obtained through imaging by the imaging optical system 200 is reconstructed by the reconstruction unit 321 based on interference signal data as three-dimensional volume data.

Specifically, the acquisition unit 310 acquires an interference signal from the line sensor 231 as 12-bit integer format data. The reconstruction unit 321 conducts wavenumber transform, fast Fourier transform (FFT), and absolute value transform (acquisition of amplitude) on this data for each point in the eye to be inspected E to generate tomographic data of the depth direction. The reconstruction unit 321 can convert and combine all the pieces of tomographic data for an area to be imaged, to thereby generate three-dimensional volume data 400.

Figure 4:
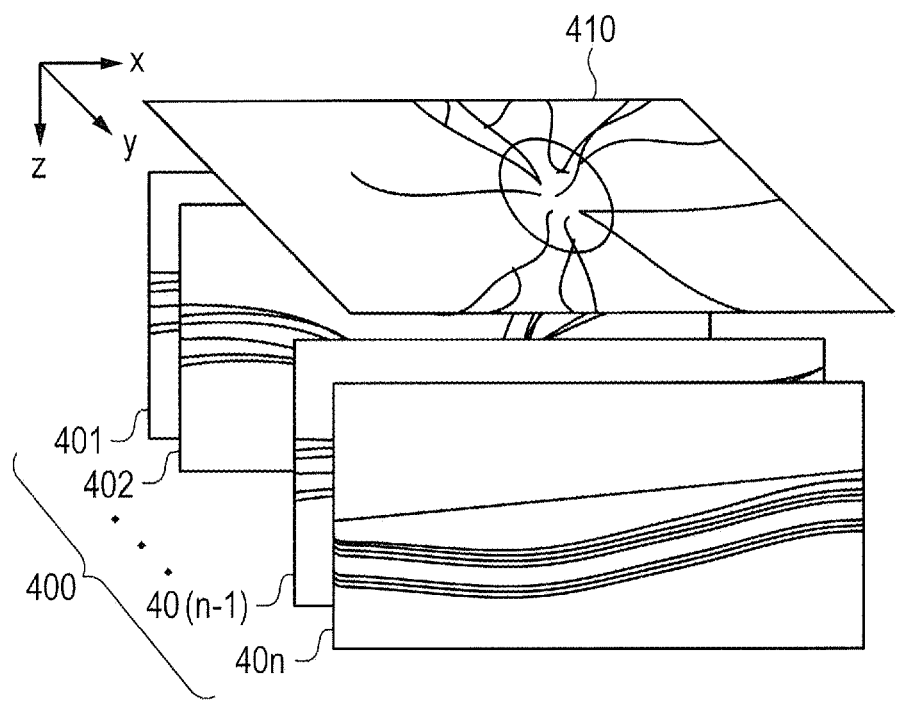
FIG. 4 is a schematic illustration of structure of three-dimensional volume data.

In this description, tomographic data on any point (x, y) in the eye to be inspected E is referred to as "A-scan data", and a set of pieces of A-scan data of a first scanning direction, which corresponds to one two-dimensional tomographic image in the three-dimensional volume data 400, is referred to as "B-scan data". In the following, B-scan data is referred to as "tomographic image data". As illustrated in FIG. 4, the three-dimensional volume data 400 corresponds to arrangement of a plurality of pieces of tomographic image data 401 to 40$n$ for each scanning position in a second scanning direction. The number "n", which is the number of pieces of tomographic image data contained in the three-dimensional volume data 400, may be set to any number depending on the desired configuration.

Now, with reference to FIG. 4, the three-dimensional volume data 400 is described in more detail. FIG. 4 is a schematic illustration of the structure of the three-dimensional volume data 400 in the first embodiment. The reconstruction unit 321 can reconstruct tomographic data, which is acquired by the imaging optical system 200 imaging the eye to be inspected E along one scanning line, to thereby generate the tomographic image data 401 corresponding to B-scan. A plane on which interference signals relating to this B-scan data are acquired is set as an xz-axis plane, and the imaging optical system 200 images the eye to be inspected E continuously in the Y-axis direction so that the reconstruction unit 321 can generate the plurality of pieces of tomographic image data 401 to 40$n$ for a particular area. Then, the reconstruction unit 321 can generate the three-dimensional volume data 400 by arranging the plurality of pieces of generated tomographic image data 401 to 40$n$ in the Y-axis direction.

The reconstruction unit 321 can generate a plurality of pieces of three-dimensional volume data 400 in a predetermined range (imaging range) of the eye to be inspected E by the imaging optical system 200 imaging the eye to be inspected E at the same location of the eye to be inspected E to acquire a plurality of pieces of B-scan data. As another method, the reconstruction unit 321 can also acquire a plurality of pieces of three-dimensional volume data by imaging an imaging range one time by dividing the acquired interference signals into a plurality of sets of interference signals based on, for example, the wavelength band, and conducting FFT processing on each set of interference signals.

Further, the image generation unit 320 can also acquire a front image 410 by generating an image on an xy-axis plane from the three-dimensional volume data 400 generated by the reconstruction unit 321. Further, as described later, the motion contrast generation unit 325 calculates a change among the plurality of pieces of three-dimensional volume data 400 to generate motion contrast data. Then, the image generation unit 320 generates the front image 410 in the xy-axis plane from the motion contrast data as an OCTA image.

The analyzation unit 322 is configured to analyze three-dimensional volume data generated by the reconstruction unit 321. More specifically, the analyzation unit 322 analyzes each of the pieces of tomographic image data 401 to 40n (or corresponding tomographic image) of the three-dimensional volume data, and detects the shape of a layer boundary that is based on a retina's layered structure of the eye to be inspected E for each of the pieces of tomographic image data 401 to 40n. The analyzation unit 322 detects 10 types of layer boundaries, namely, ILM, NFL/GCL, GCL/IPL, IPL/INL, INL/OPL, OPL/ONL, IS/OS, OS/RPE, RPE/Choroid, and BM. The layer boundary to be detected is not limited thereto, and may be changed depending on the desired configuration.

Further, a method of detecting the layer boundary may be performed by any known method. For example, the analyzation unit 322 applies each of the median filter and Sobel filter to a tomographic image, which corresponds to tomographic image data, to generate images (hereinafter referred to as "median image" and "Sobel image", respectively). Next, the analyzation unit 322 generates a profile for each piece of data, which corresponds to A-scan data, from the generated median image and Sobel image. The generated profile is a luminance value profile for the median image and a gradient profile for the Sobel image. Then, the analyzation unit 322 detects a peak in the profile generated from the Sobel image. The analyzation unit 322 refers to the profile for the median image corresponding to a part before/after the detected peak and a part between the detected peaks, to thereby detect and extract the boundary of each area of the retina's layers.

The target acquisition unit (second acquisition unit) 323, the data correction unit 324, and the motion contrast generation unit 325 function to generate motion contrast data. The target acquisition unit 323 is configured to acquire a target distribution of tomographic data to be corrected by the data correction unit 324. In the first embodiment, the target acquisition unit 323 acquires the target stored in the storage 340 in advance. The target can be set from, for example, past inspection results for each subject to be examined and statistical data on a plurality of subjects to be examined.

The data correction unit (correction unit) 324 is configured to correct the distribution of tomographic data, which is contained in the three-dimensional volume data generated by the reconstruction unit 321, as pre-processing before generation of the motion contrast data. The method for correction is described later.

The motion contrast generation unit 325 is configured to first correct, for each piece of tomographic image data, positional deviation between a plurality of pieces of three-dimensional volume data imaged in the same range of the eye to be inspected E. The method of correcting positional deviation may be any method.

For example, the motion contrast generation unit 325 images the same range M times, and aligns positions for pieces of tomographic image data on the same location in the acquired M pieces of three-dimensional volume data using, for example, characteristics including a fundus shape. Specifically, one out of M pieces of tomographic image data is selected as a template, and a similarity with the other tomographic image data is calculated while changing the position and angle of the template to acquire an amount of positional deviation with respect to the template. After that, the motion contrast generation unit 325 corrects each piece of tomographic image data based on the acquired amount of positional deviation, and corrects positional deviation between M pieces of three-dimensional volume data.

Next, the motion contrast generation unit 325 calculates a decorrelation value Mxy by Expression (1) between two pieces of tomographic image data of the three-dimensional volume data, which are continuous in time of imaging of the two pieces of tomographic image data.

$$Mxy = 1 - 2 \times \frac{Axy \times Bxy}{Axy^2 + Bxy^2} \qquad \text{Expression (1)}$$

In Expression (1), Axy represents a luminance at a position (x, y) of the tomographic image data A, and Bxy represents a luminance at the same position (x, y) of the tomographic image data B. It suffices that the corresponding two pieces of three-dimensional volume data for calculating the decorrelation value Mxy have imaging times that fall within a predetermined interval, and the imaging times may not be continuous.

The decorrelation value Mxy takes a value of from 0 to 1, and as a difference between two luminances becomes larger, the value of Mxy becomes larger. The motion contrast generation unit 325 can calculate the plurality of decorrelation values Mxy from three or more pieces of three-dimensional volume data that are acquired at the same location repeatedly. The motion contrast generation unit 325 can conduct statistical processing such as maximum value calculation or average calculation of the plurality of calculated decorrelation values Mxy, to thereby generate definitive motion contrast data.

Meanwhile, the formula for calculating the motion contrast shown in Expression (1) is susceptible to noises. For example, when the plurality of pieces of tomographic image data have noises in non-signal parts, and thus have different values, the decorrelation value becomes higher and the motion contrast image also has noises.

In order to address this issue, the motion contrast generation unit 325 can regard a piece of tomographic data that falls below a predetermined threshold Dth as noises to replace the piece of tomographic data with zero as pre-processing. In the following, the value Dth is referred to as "noise threshold". Further, the processing of replacing the piece of tomographic data that falls below the noise threshold Dth with zero is referred to as "noise mask processing". With this, the image generation unit 320 can generate a motion contrast image that has reduced the influence of noises based on the generated motion contrast data. An example of the method of calculating the noise threshold Dth is to calculate Dth=BGa+2σ, where BGa represents an average value of luminances over the entire B-scan data, which is obtained by imaging under a state of no object to be inspected, and σ represents a standard deviation of the luminance values over the entire B-scan data. Alternatively, any known method of calculating the noise threshold can be used.

The drive control unit 330 is configured to drive the components of the imaging optical system 200, such as the SLO optical source 210, the SLO scanning unit 204, the OCT light source 220, and the XY scanner 216. The storage 340 is configured to store, for example, various images generated by the image generation unit 320, input information on the subject to be examined, and programs for configuring the control unit 300. The display control unit 350 is configured to control the display unit 500, and causes various images stored in the storage 340 and information on the subject to be examined to be displayed on the display unit 500.

The components of the control unit 300 can be configured by modules to be executed by a CPU or MPU of the control unit 300. Alternatively, the components of the control unit 300 may be configured by, for example, a circuit that implements a specific function, for example, ASIC. The storage 340 may be configured by using any storage device or storage medium such as a memory or an optical disc.

(Configuration of User Interface)

Figure 5:
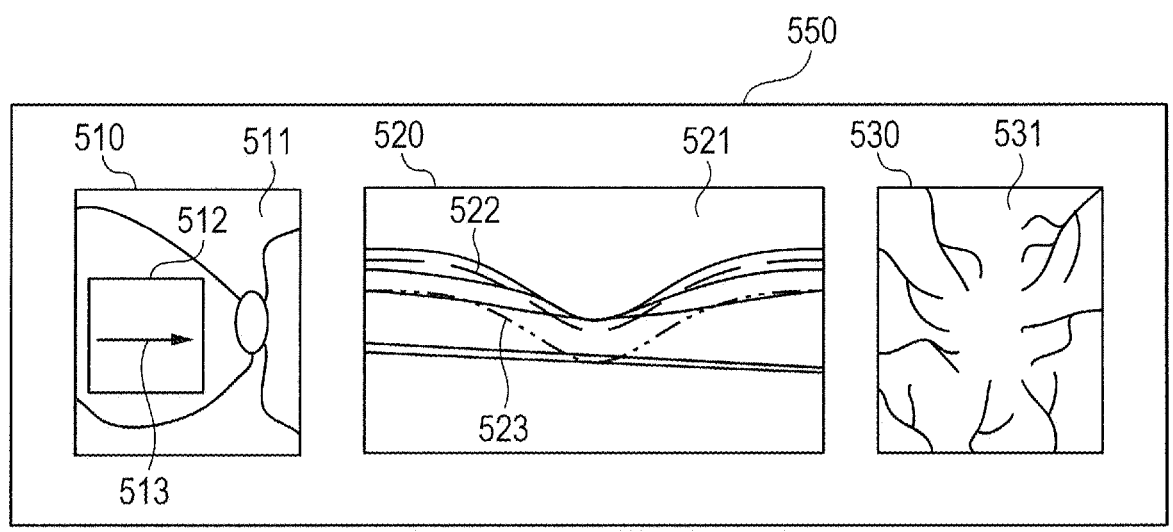
FIG. 5 is an illustration of an exemplary user interface in the first embodiment.

Now, with reference to FIG. 5, the configuration of a user interface for generating an OCTA image in the first embodiment is described. FIG. 5 is an illustration of an example of the user interface to be displayed at the time of generation of an OCTA image.

After the imaging optical system 200 finishes imaging the eye to be inspected E, the display unit 500 displays a user interface 550 for generating an OCTA image on the screen. Three display areas, namely, a fundus image display area 510, a tomographic image display area 520, and an OCTA image display area 530 are provided on the user interface 550.

A fundus image 511 of the eye to be inspected E is displayed on the fundus image display area 510. An imaging area annotation 512 and a cross section position annotation 513 are displayed on the fundus image 511. The imaging area annotation 512 represents an area imaged by the imaging optical system 200 that has acquired an interference signal corresponding to three-dimensional volume data. In the first embodiment, an SLO image obtained by using the imaging optical system 200 is displayed as the fundus image 511. However, a fundus image imaged by a fundus image imaging apparatus other than the imaging optical system 200 may be displayed as the fundus image 511. In that case, the position of the imaging area annotation is aligned with the fundus image, and is displayed at an appropriate position.

The cross section position annotation 513 represents a position on the fundus image 511 of a tomographic image 521 to be displayed on the tomographic image display area 520. An operator can move the cross section position annotation 513 via the input unit 360 to determine a position on the eye to be inspected E of the tomographic image 521 to be displayed on the tomographic image display area 520. The image generation unit 320 generates the tomographic image 521 corresponding to the determined position based on the three-dimensional volume data.

The tomographic image 521 corresponding to the position of the cross section position annotation 513 is displayed on the tomographic image display area 520. A generation range upper limit 522 and a generation range lower limit 523 for specifying a range of generation of an OCTA image is displayed on the tomographic image 521. In FIG. 5, the generation range upper limit 522 is indicated by the broken line, and the generation range lower limit 523 is indicated by a chain double-dashed line.

The control unit 300 projects motion contrast data of a range corresponding to a range between the generation range upper limit 522 and the generation range lower limit 523, which is a specified depth range, onto a two-dimensional plane, to thereby generate an OCTA image. Specifically, the image generation unit 320 generates an OCTA image, which is a front image of the motion contrast image, based on motion contrast data corresponding to the range between the generation range upper limit 522 and the generation range lower limit 523 among the entire motion contrast data. The motion contrast generation unit 325 may be configured to generate the motion contrast data using tomographic data of the range between the generation range upper limit 522 and the generation range lower limit 523. In this case, the image generation unit 320 can generate an OCTA image based on the generated motion contrast data, to thereby generate the OCTA image that is based on the tomographic data of the specified depth range.

The operator can determine the positions of the generation range upper limit 522 and the generation range lower limit 523 via the input unit 360. Shapes of the generation range upper limit 522 and the generation range lower limit 523 can be specified by a specific layer shape or a straight line, or freehand. Further, the positions of the generation range upper limit 522 and the generation range lower limit 523 can also be set freely, that is, may be moved freely, set to specific positions or layers, or set to have any distances from those specific positions or layers, via the input unit 360. Further, ranges of generation of an OCTA image may be set in advance for selection.

An OCTA image 531 generated based on tomographic data between the generation range upper limit 522 and the generation range lower limit 523 of the specified OCTA image is displayed on the OCTA image display area 530.

As described above, the operator can use the user interface 550 to determine tomographic data to be used for generating the OCTA image. More specifically, the operator specifies the position of the cross section position annotation 513, and then determines the range of tomographic data to be used for generating the OCTA image 531 in the tomographic image display area 520. After that, the OCTA image 531 generated based on the determined tomographic data is displayed on the OCTA image display area 530.

In the above, the operator has determined tomographic data to be used for generating the OCTA image. However, the method of determining tomographic data serving as a source for generating an OCTA image is not limited thereto. For example, the control unit 300 may determine tomographic data to be used for generating an OCTA image based on information on an inspection part set in advance, past inspection details of the subject to be examined, and an imaging mode. In this case, the control unit 300 can determine the range of tomographic data to be used for generating an OCTA image based on the layer detected by the analyzation unit 322.

(Flow of Generation of OCTA Image in First Embodiment)

Next, a flow of generation of an OCTA image in the first embodiment is described with reference to FIG. 6 to FIG. 7C. FIG. 6 is a flowchart of OCTA image generation processing in the first embodiment.

An interference signal acquired by the imaging optical system 200 may have a partially low signal strength when the state of the eye to be inspected E or the imaging condition is not optimal. When the signal strength is low, the reconstructed tomographic image becomes a dark image, and the OCTA image also has a dark part. Thus, in the OCTA image generation processing in the first embodiment, the data correction unit 324 corrects the distribution of a parameter of the tomographic data to be used for calculating motion contrast data, which is contained in the three-dimensional volume data, so that the distribution becomes closer to an ideal target distribution. The control unit 300 generates an OCTA image, which is a front image of the motion contrast image, based on the corrected tomographic data, to thereby be able to generate the OCTA image that has suppressed occurrence of contrast due to deviation of a tomographic signal. In the first embodiment, the data correction unit 324 performs correction for each distribution of A-scan data contained in the three-dimensional volume data.

Specifically, when the OCTA image generation processing is started, in Step S601, the acquisition unit 310 acquires three-dimensional volume data from the reconstruction unit 321. As described above, the three-dimensional volume data is generated by the reconstruction unit 321 based on the interference signal acquired by the imaging optical system 200.

In Step S602, the target acquisition unit 323 acquires, from the storage 340, a target for correcting the tomographic data with the data correction unit. The target may be acquired from other apparatus connected to the control unit 300. In this case, as described above, the target can be set from, for example, past inspection results for each subject to be examined and statistical data on a plurality of subjects to be examined.

In Step S603, the data correction unit 324 extracts the distribution of a parameter to be used for calculating motion contrast data of tomographic data to be corrected, from the three-dimensional volume data. In the first embodiment, the luminance value of tomographic data corresponding to the amplitude of Fourier transformed complex number data is used as the parameter to be used for calculating motion contrast data. The data correction unit 324 calculates the distribution of luminance values for each piece of A-scan data contained in the three-dimensional volume data in order to correct the distribution of each piece of A-scan data contained in the three-dimensional volume data. The parameter to be used for calculating motion contrast data is not limited to the luminance value, and may be, for example, a phase value or both of the luminance value and phase value depending on the method of calculating motion contrast data.

Figure 7A:
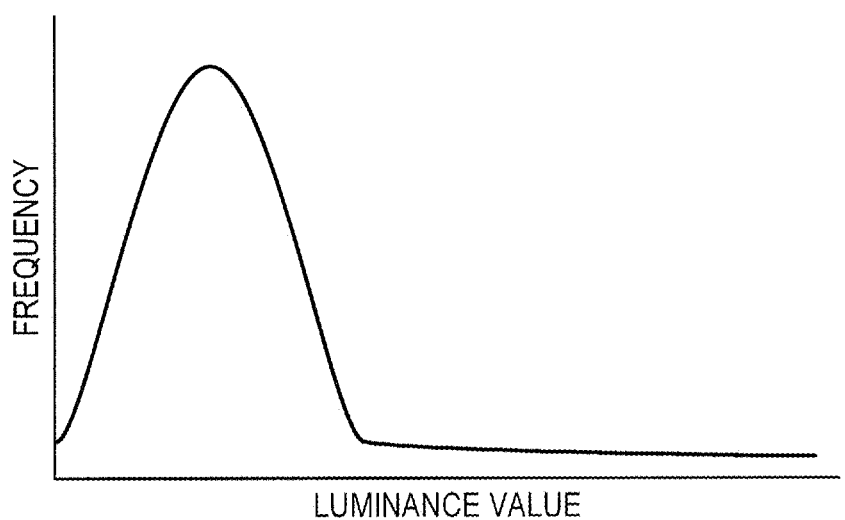
FIG. 7A is a graph for showing data distribution in the first embodiment.
Figure 7B:
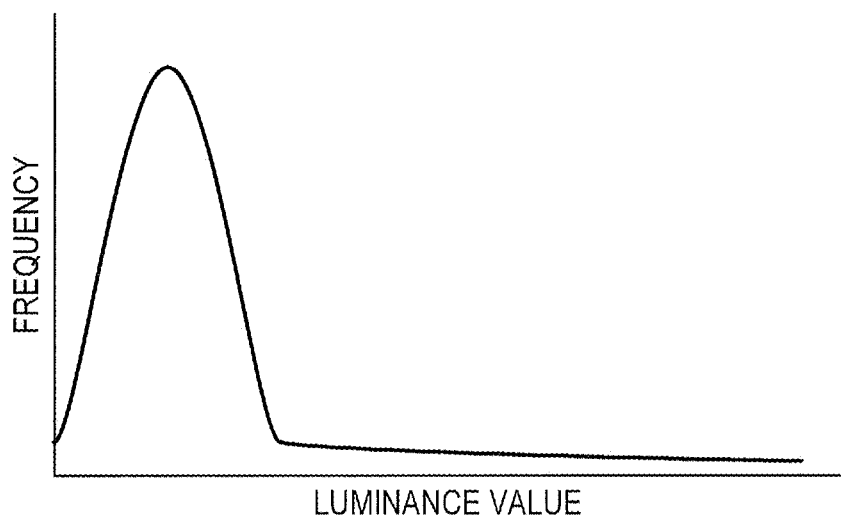
FIG. 7B is a graph for showing data distribution in the first embodiment.
Figure 7C:
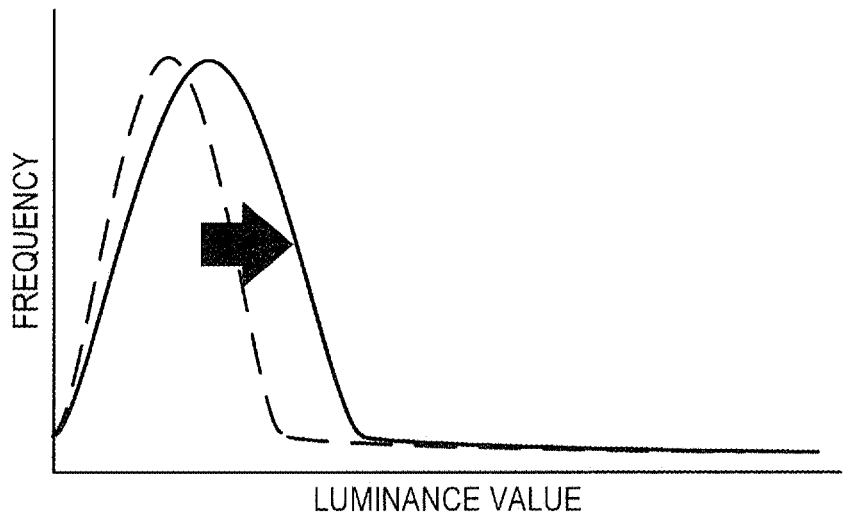
FIG. 7C is a graph for showing data distribution in the first embodiment.

FIG. 7A to FIG. 7C are graphs for showing histograms of A-scan data contained in the three-dimensional volume data. In FIG. 7A to FIG. 7C, the horizontal axis represents a luminance value, and the vertical axis represents the frequency of each luminance. FIG. 7A and FIG. 7B are schematic illustrations of examples of the histogram of A-scan data in a case where the signal strength of an interference signal is sufficiently high and in a case where the signal strength of an interference signal is low, respectively. In the following, for the sake of description, the histogram of A-scan data to be corrected is the histogram illustrated in FIG. 7B, and the histogram of A-scan data to be a target is the histogram illustrated in FIG. 7A.

In Step S604, as indicated by the arrow of FIG. 7C, the data correction unit 324 corrects the distribution of A-scan data to be corrected, which is indicated by the broken line, so that the distribution of A-scan data to be corrected becomes closer to the target indicated by the solid line.

The data correction unit 324 transforms the distribution of each piece of A-scan data so that an average value $Av\_0$ and a standard deviation $\sigma 0$ of each piece of A-scan data become closer to an average value $Av\_t$ and a standard deviation $\sigma t$ of the target A-scan data acquired by the target acquisition unit 323. Specifically, the data correction unit 324 performs transformation so that the distribution of relevant A-scan data becomes closer to the distribution of target A-scan data by Expression (2) given below.

$$y=(x-Av\_0) \times Ga + (Av\_0 \times Gb)$$

$$Ga = \sigma t / \sigma 0$$

$$Gb = Av\_t / Av\_0 \quad \text{Expression (2)}$$

In Expression (2), y represents corrected A-scan data, and x represents uncorrected A-scan data.

The data correction unit 324 can calculate Expression (2) to transform the uncorrected distribution of A-scan data into the distribution having an average value and a standard deviation of the target A-scan data.

Next, in Step S605, the motion contrast generation unit 325 uses the corrected tomographic data to generate motion contrast data as described above.

In Step S606, the image generation unit 320 generates an OCTA image, which is a front image of the motion contrast image, based on the generated motion contrast data. Through the OCTA image generation processing, the control unit 300 generates an OCTA image based on the corrected tomographic data, and thus it is possible to obtain a high-definition OCTA image without being influenced by partial contrast of the tomographic image.

In the first embodiment, the target is acquired (Step S602) after the three-dimensional volume data is acquired (Step S601), but it suffices that the target is acquired before correction (Step S604) of the data distribution. Thus, the target may be acquired after extraction (Step S603) of the data distribution, or may be acquired at the same time as acquisition (Step S601) of the three-dimensional volume data or extraction (Step S603) of the data distribution.

As described above, the control unit 300 in the first embodiment includes the acquisition unit 310, the target acquisition unit 323, the data correction unit 324, and the image generation unit 320. The acquisition unit 310 acquires a plurality of pieces of tomographic data each representing information on a cross section of the fundus, which is acquired based on the measurement light controlled to scan the same position of the fundus of the eye to be inspected E. The target acquisition unit 323 acquires the target distribution of a parameter of the tomographic data to be used for calculating a motion contrast. In the first embodiment, the luminance of tomographic data is used as the parameter. The target acquisition unit 323 acquires, as the target, a predetermined distribution defined for each subject to be examined or statistically defined for the plurality of subjects to be examined. The data correction unit 324 performs correction so that the distribution of the parameter of at least one piece of tomographic data among a plurality of pieces of tomographic data becomes closer to the target. The image generation unit 320 generates a motion contrast image based on the motion contrast calculated using the plurality of pieces of tomographic data including at least one piece of tomographic data corrected by the data correction unit 324.

The control unit 300 performs correction so that the distribution of parameters of tomographic data, which is source data for generating the motion contrast, becomes closer to the target. Thus, the contrast for each parameter is suppressed. Therefore, it is possible to suppress the contrast of an OCTA image due to deviation of tomographic data to be used for calculating a motion contrast, to thereby obtain a high-definition OCTA image.

When the average value and standard deviation of A-scan data to be corrected are significantly low compared to the target at the time of correction with the method described above, values of gains Ga and Gb in Expression (2) become larger, and noises may be conspicuous in the OCTA image. Further, when the average value and standard deviation of A-scan data to be corrected are significantly high compared to the target, a vascular network in the OCTA image may be unclear. To address this issue, upper limits and lower limits of the gains Ga and Gb can be set so that those gains Ga and Gb are replaced with the upper limits and lower limits when exceeding those upper limits and lower limits.

Further, in the first embodiment, the example of correction for each piece of A-scan data is given, but data to be corrected is not limited thereto. For example, B-scan data or the distribution over the entire three-dimensional volume data may be corrected to become closer to the target distribution. Alternatively, the distribution of a set of a plurality of continuous pieces of A-scan data obtained by dividing the B-scan data in a strip form may be corrected, or the distribution of a set of a plurality of similar consecutive pieces of B-scan data may be corrected. Alternatively, for example, a plurality of pieces of three-dimensional volume data to be used for generating motion contrast data may be combined to obtain an averaged distribution for correction. Alternatively, a plurality of pieces of tomographic images that can be generated by using split-spectrum amplitude-decorrelation angiography (SSADA), which is one motion contrast data generation method, may be used to obtain a distribution for correction. The distribution of tomographic data is herein assumed to include those distributions. In those cases, the target distributions are also assumed to be distributions corresponding to distributions of those pieces of tomographic data such as distributions of B-scan data, three-dimensional volume data, and a set of a plurality of continuous pieces of A-scan data. Also through execution of such a method, the control unit 300 can suppress contrast in the OCTA image due to deviation of tomographic data, to thereby generate a high-definition OCTA image. Further, through correction of a relatively wide range of pieces of data in bulk, it is possible to reduce overcorrection of the tomographic data compared to local correction.

Further, in the first embodiment, the distribution of each piece of A-scan data contained in the three-dimensional volume data is corrected, but data to be corrected is not limited thereto. For example, only the distribution of A-scan data for which the statistical value of luminances contained in the A-scan data is smaller than a predetermined threshold may be corrected among pieces of A-scan data contained in the three-dimensional volume data. The statistical value may be, for example, a sum, an average value, a median, a maximum value, a variance, a mode, or a combination thereof. When data to be corrected is a distribution of, for example, B-scan data, the data correction unit 324 can correct only the distribution of data to be corrected for which the statistical value of luminances contained in the data to be corrected is smaller than a predetermined threshold depending on units (e.g., B-scan data) of the data to be corrected. Not only the lower limit threshold but also the upper limit threshold may be set to perform correction when the upper limit value is exceeded, depending on the desired configuration.

Further, only when the data correction unit 324 compares the distribution of A-scan data, which is potential data to be corrected, with the target distribution and a difference between statistical values of distributions is larger than a predetermined threshold, the distribution of the relevant A-scan data may be corrected. As the difference between statistical values of distributions, for example, at least one difference may be taken from among average values, maximum values, modes, variances, or frequency widths in the distributions of pieces of tomographic data to be compared. In this case, the data correction unit 324 corrects only the tomographic data for which the distribution is different from the target distribution by a certain value or more. Therefore, it is possible to reduce the amount of calculation required for correction and shorten the processing time. The data correction unit may compare the distribution of A-scan data, which is potential data to be corrected, with the distribution of tomographic data serving as a template freely selected from pieces of three-dimensional volume data as well as the target distribution. The tomographic data serving as the template in this case can be set to, for example, a piece of three-dimensional volume data for which the average value of luminances is higher than the average value of luminances of the entire three-dimensional volume data, or a piece of three-dimensional volume data for which the luminance value is the highest in the entire three-dimensional volume data.

Further, in the first embodiment, the data correction unit 324 corrects the distribution of the entire A-scan data, but may correct the distribution of only the A-scan data that relates to the depth range of the retina analyzed by the analyzation unit 322. Further, the data correction unit 324 may correct the distribution of A-scan data of the range between the generation range upper limit 522 and the generation range lower limit 523.

Further, imaging by OCT cannot achieve accurate imaging at a desired position, for example, when the eye to be inspected E has moved during imaging, and thus the desired position may be scanned again. In this case, the imaging situation at the time of re-scanning changes from the imaging situation at the time of original scanning, and brightness of the tomographic image may have contrast. In view of this, the correction processing in the first embodiment may be conducted only on the part to be scanned again as a measure to prevent re-scanning from causing contrast in brightness of the tomographic image. Also in this case, data to be corrected is not limited to the distribution of A-scan data, but may be the distribution of B-scan data, distributions of a plurality of pieces of A-scan data or B-scan data containing the part to be scanned again, or the distribution of other tomographic data described above.

In the first embodiment, the target average value and standard deviation are set to correct the average value and standard deviation of the distribution of A-scan data so that the average value and standard deviation become closer to the target, but data to be corrected to become closer to the target is not limited thereto. For example, the standard deviation may be maintained, whereas only the average is corrected. Further, at least one of the average value, the maximum value, the mode, the variance, or the frequency width may be corrected to become closer to the target. The target may be input from the outside of the control unit 300 and set without setting the target as a value prepared in advance.

Second Embodiment

In the first embodiment, the data correction unit 324 corrects the average value and standard deviation of the entire distribution of relevant A-scan data so that the average value and standard deviation become closer to the target average value and standard deviation. In contrast, in a second embodiment of this disclosure, parts excluding no-signal parts of the distribution of relevant A-scan data are data to be corrected. In the following, with reference to FIG. 8A to FIG. 8C, the control unit in the second embodiment is described. Components of the control unit in the second embodiment are similar to those of the control unit 300 in the first embodiment, and thus the same reference numerals are used to omit descriptions thereof. In the following, the control unit in the second embodiment is described with emphasis on a difference from the control unit 300 in the first embodiment.

Figure 8A:
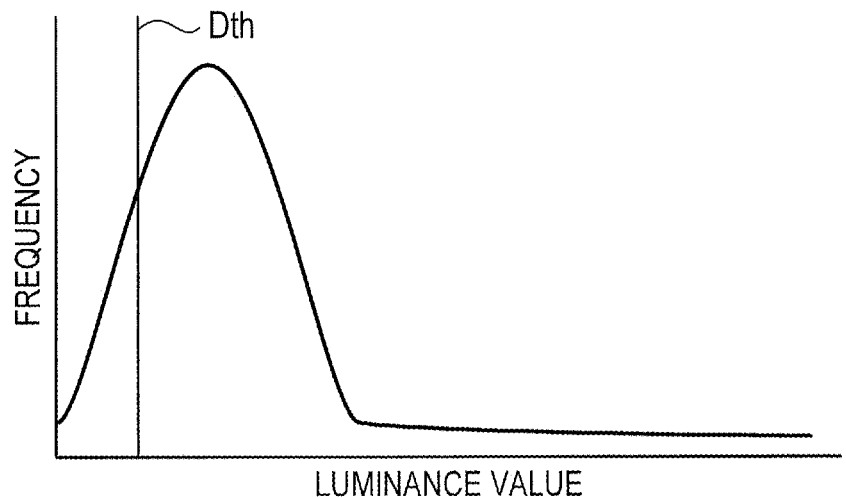
FIG. 8A is a graph for showing data distribution in a second embodiment of this disclosure.
Figure 8B:
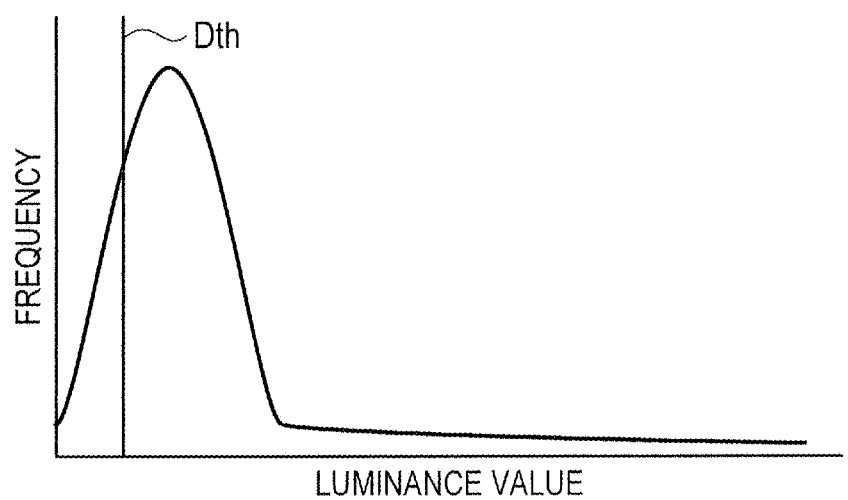
FIG. 8B is a graph for showing data distribution in the second embodiment.
Figure 8C:
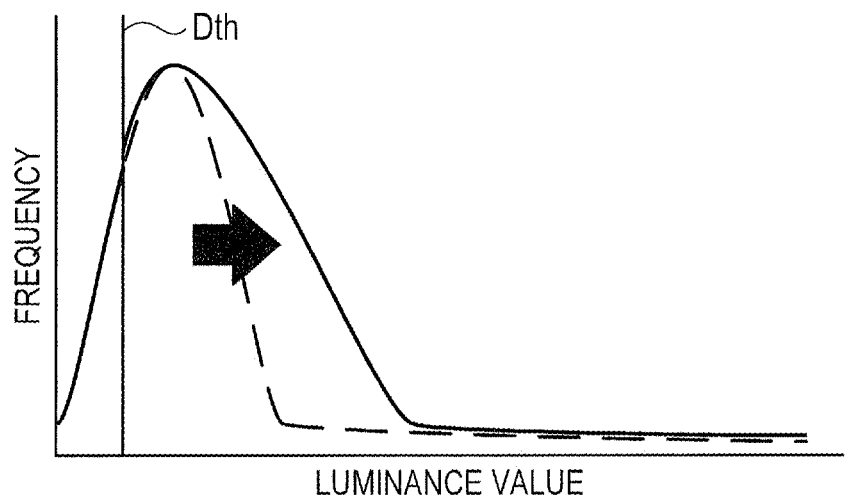
FIG. 8C is a graph for showing data distribution in the second embodiment.

FIG. 8A to FIG. 8C are graphs for showing data to be corrected in the second embodiment. FIG. 8A to FIG. 8C correspond to FIG. 7A to FIG. 7C, respectively. Further, the noise threshold Dth is shown in FIG. 8A to FIG. 8C to describe data to be corrected in the second embodiment. In FIG. 8A to FIG. 8C, the horizontal axis represents the luminance value, and the vertical axis represents the frequency of each luminance.

Imaging of a cross section of the retina results in a large number of no-signal parts being contained in the acquired tomographic data. Such no-signal parts contain noises. As described above, when the tomographic data contains noises, the motion contrast that is based on tomographic data also represents noise parts as a temporal change in measurement target. At this time, when the data correction unit also corrects noise parts contained in the tomographic data, noises contained in those noise parts may be amplified. In this case, the OCTA image that is based on corrected data also increases noises. In view of the above, in the second embodiment, parts other than no-signal parts in the distribution of tomographic data are data to be corrected, and the distribution of noise parts is corrected to prevent noises from being amplified.

The data correction unit 324 in the second embodiment sets the average value Av_t of target A-scan data for the distribution of relevant A-scan data, and corrects the distribution of each piece of A-scan data so that the distribution of each piece of A-scan data becomes closer to the target. In that case, as shown in FIG. 8C, only the data on luminance values equal to or larger than the noise threshold Dth is corrected in accordance with Expression (3) given below.

$$\begin{cases} y = x & : x < Dth \\ y = (x - Dth) \times A + Dth & : x \geq Dth \end{cases} \quad \text{Expression (3)}$$

$$A = (Av\_t - Dth)/(Av\_0 - Dth)$$

The data correction unit 324 can perform correction in this manner so that values equal to or larger than the noise threshold Dth are transformed into data having a target average distribution without changing values smaller than the noise threshold Dth in the distribution of uncorrected A-scan data. Thus, the control unit in the second embodiment can prevent correction of data from increasing noises in the OCTA image.

As described above, the data correction unit 324 in the second embodiment corrects the distribution of parameter parts having values equal to or larger than the noise threshold in the distribution of parameters of tomographic data. The control unit can generate motion contrast data based on the tomographic data corrected in this manner, to suppress influences of brightness of a tomographic image on the OCTA image without amplifying noises, to thereby obtain a higher definition OCTA image. Signals smaller than the noise threshold may be excluded from calculation of motion contrast data.

The noise threshold Dth may be stored in the storage 340 in advance for each imaging optical system 200 (each imaging apparatus) configured to image a cross section of the eye to be inspected E, or may be set based on background data obtained by blocking the measurement light at the time of activation or at the time of start of imaging by the imaging optical system 200. Further, the noise threshold Dth may be set based on any one of the value of a parameter used to calculate motion contrast data and the frequency of the parameter of tomographic data contained in a plurality of pieces of three-dimensional volume data. In this case, for example, the data correction unit 324 may set, as the threshold, the value of a parameter of tomographic data to be corrected or a lower 10 percentile of the frequency. The value of the lower 10 percentile is just an example, and may be set freely depending on the desired configuration.

Further, similarly to the first embodiment, data to be corrected by the data correction unit 324 is not limited to A-scan data, and for example, B-scan data or three-dimensional volume data may be corrected.

Third Embodiment

In the first embodiments and the second embodiment, the data correction unit 324 corrects the distribution of tomographic data so that the average value and standard deviation thereof become closer to the target average value and standard deviation set in advance. In contrast, in a third embodiment of this disclosure, the target average value and standard deviation are calculated from the three-dimensional volume data generated by the reconstruction unit 321, and the distribution of tomographic data is corrected so as to become closer to the calculated target. In the following, with reference to FIG. 9, the control unit in the third embodiment is described. Components of the control unit in the third embodiment are similar to the control unit 300 in the first embodiment, and thus the same reference numerals are used to omit descriptions thereof. In the following, the control unit in the third embodiment is described with emphasis on a difference from the control unit 300 in the first embodiment.

Figure 9:
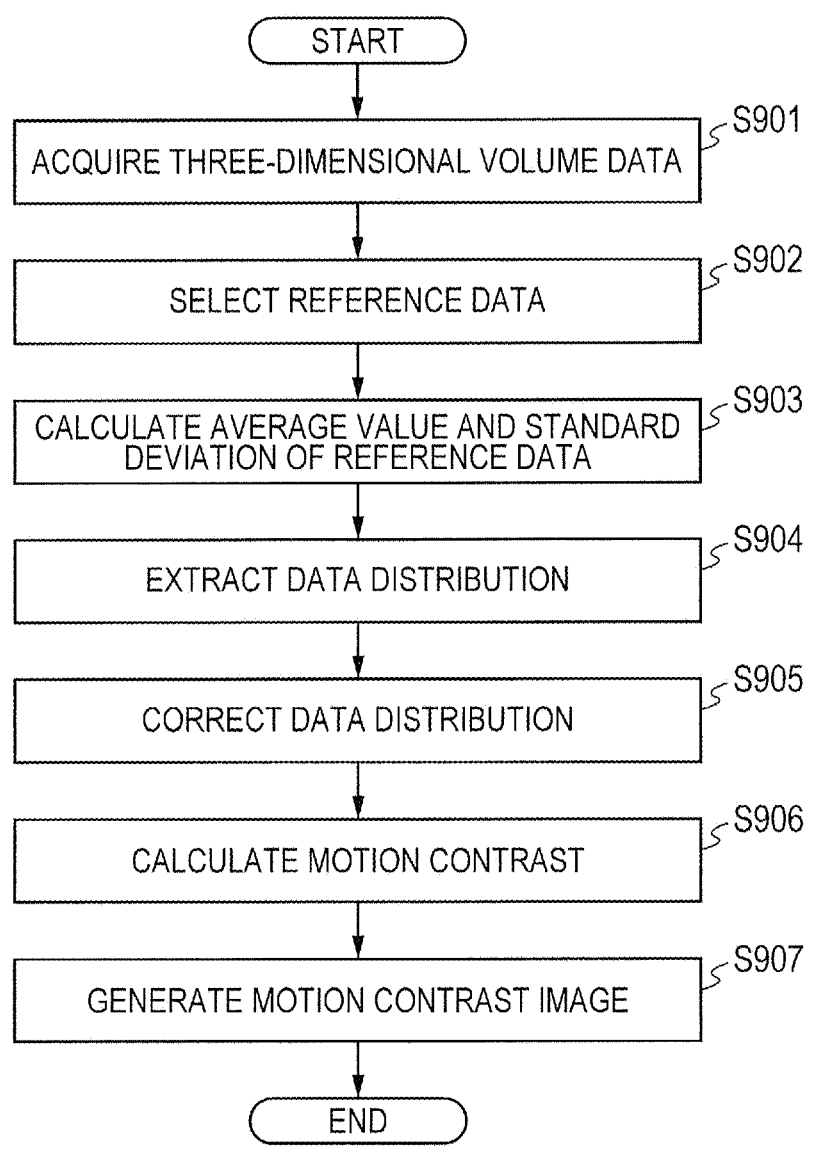
FIG. 9 is an illustration of a flow of OCTA image generation processing in a third embodiment of this disclosure.

FIG. 9 is a flowchart for illustrating OCTA image generation processing in the third embodiment of this disclosure. Steps other than Step S902 and Step S903 in the flowchart illustrated in FIG. 9 are similar to those of the OCTA image generation processing in the first embodiment, and thus a description thereof is omitted here.

In Step S901, when the acquisition unit 310 acquires three-dimensional volume data, the processing advances to Step S902. In Step S902, the target acquisition unit 323 selects, as reference data, B-scan data from which B-scan data having a low signal strength is excluded from the three-dimensional volume data. In the third embodiment, B-scan data for which the average value of luminances of the retina part (from ILM to BM) is larger than the average value of luminances of the entire retina part in three-dimensional volume data is selected as reference data.

First, the target acquisition unit 323 calculates the average value of luminances of from ILM to BM of each piece of A-scan data contained in the three-dimensional volume data in accordance with Expression (4). A_av(x, y) represents the average value of luminances of an x-th A-scan in a y-th B-scan. Each depth data Z(i, x, y) in each piece of A-scan is added for a range of from a position Pilm(x, y) of ILM to a position Pbm(x, y) of BM. The sum is divided by the number of pieces of data to calculate A_av(x, y). The symbol i represents an index of the depth position.

$$A\_av(x, y) = \frac{\sum_{i=Pilm(x,y)}^{Pbm(x,y)} Z(1, x, y)}{Pbm(x, y) - Pilm(x, y) + 1} \quad \text{Expression (4)}$$

Next, the target acquisition unit 323 calculates the average value of luminances of each piece of B-scan data in accordance with Expression (5). B_av(y) represents an average value of luminances of y-th B-scan data in the three-dimensional volume data. The average values of luminances of all the pieces of A-scan data in the y-th B-scan data calculated by Expression (4) are added and then divided by the number m of pieces of A-scan data to calculate B_av(y).

$$B\_av(y) = \frac{\sum_{i=1}^{m} A\_av(1, y)}{m} \qquad \text{Expression (5)}$$

Further, the target acquisition unit 323 calculates an average value Av_all of luminances of from ILM to BM of the entire three-dimensional volume data in accordance with Expression (6). The average values of luminances of all the B-scans in the three-dimensional volume data calculated by Expression (5) are added and then divided by the number n of B-scans in the three-dimensional volume data to calculate Av_all.

$$Av\_all = \frac{\sum_{k=1}^{n} B(k)}{n} \qquad \text{Expression (6)}$$

Lastly, when Expression (7) is satisfied, namely, when the average value B_av(y) of pieces of B-scan data is larger than the average value Av_all of the entire three-dimensional volume data, the target acquisition unit 323 selects the B-scan as reference data.

$$B\_av(y) > Av\_all \qquad \text{Expression (7)}$$

With this, B-scan data having a low signal strength is excluded from n pieces of B-scan data contained in the three-dimensional volume data, and the left pieces of B-scan data can be selected as reference data. In particular, the luminance value of only the retina part can be used for the above-mentioned calculation to select reference data without B-scan data having a larger number of non-retina parts such as macula or optic papilla being excluded.

Next, in Step S903, the target acquisition unit 323 calculates the target average value Av_t and standard deviation σ_t of A-scan data using the B-scan data selected as reference data. The target acquisition unit 323 divides the sum of average values B_av' of luminances of respective selected pieces of B-scan data by the number s of selected B-scans in accordance with Expression (8), to thereby calculate the target average value Av_t.

$$Av\_t = \frac{\sum_{i=1}^{s} B\_av'(1)}{s} \qquad \text{Expression (8)}$$

Further, the target acquisition unit 323 subtracts the average value Av_t calculated by Expression (8) from each average value of the luminances of each piece of B-scan data selected as reference data, takes the square of each difference, adds all of the squares, and divides the sum by the number s of selected B-scans, to thereby calculate a standard deviation δ_t in accordance with Expression (9).

$$\sigma\_t = \sqrt{\frac{\sum_{i=1}^{s} (B\_av'(1) - Av\_t)^2}{s}} \qquad \text{Expression (9)}$$

In this manner, the target acquisition unit 323 calculates the target average value Av_t and standard deviation σ_t. When the target average value Av_t and standard deviation σ_t are calculated, the processing advances to Step S904. The processing after Step S904 is similar to the processing in the first embodiment, and thus a description thereof is omitted here.

The average value Av_t and standard deviation σ_t can be calculated by the target acquisition unit 323 using data of the same range as data used for correction (S905) of the data distribution to be executed later. For example, when the data correction unit 324 corrects the distribution of tomographic data of only the retina part, the average value and standard deviation of the retina part can be calculated, or when the data correction unit 324 corrects the distribution including non-retina parts, the entire average value and standard deviation including non-retina parts can be calculated.

Further, the steps (Step S902 and Step S903) of calculating the target may be performed at the same time as or after the step (Step S904) of extracting the data distribution.

In this manner, the target acquisition unit 323 in the third embodiment sets the target based on tomographic data on at least one piece of a plurality of pieces of three-dimensional volume data. The control unit in the third embodiment corrects the distribution of A-scan data so that the distribution becomes closer to the set target (average value Av_t and standard deviation σ_t). In this case, the distribution of tomographic data in three-dimensional volume data is corrected with the ideal distribution of data having a high signal strength in the same three-volume data being set as the target, to thereby suppress contrast of each piece of tomographic data in the three-dimensional volume data. Therefore, the control unit can generate an OCTA image that has suppressed occurrence of contrast due to deviation in tomographic data. Further, the target is obtained from the acquired three-dimensional volume data, to thereby be able to effectively correct a change in tomographic data due to a diseased eye or an imaging condition in such a manner as to suit a more realistic condition.

When the correction method in the second embodiment is applied to the OCTA image generation processing in the first embodiment, the average value Av_t and standard deviation σ_t of tomographic data having a luminance equal to or larger than the noise threshold Dth are calculated and corrected, to thereby be able to set a target more appropriate for data to be corrected.

Further, in selection of B-scan data in the third embodiment, the average value of luminances of the retina part is calculated, but the average value of luminances may be calculated from a specific layer in the retina or from the entire A-scan data including non-retina parts.

Further, in the third embodiment, B-scan data having a luminance value larger than an average value of luminances of all the retina parts in the three-dimensional volume data is selected as reference data. However, the method of selecting reference data is not limited thereto, and for example, B-scan data having a larger luminance value may be selected. Further, the luminance distribution may be acquired to select B-scan data having the most dense luminance distribution. With those methods too, it is possible to select tomographic data on a part that does not include tomographic data having a low signal strength. Alternatively, as a countermeasure to prevent occurrence of contrast in brightness of a tomographic image by re-scanning, reference data may be selected from only the re-scanned part or the originally scanned part.

Further, in the third embodiment, B-scan data having an average value of luminances larger than the average value of all the luminances in the three-dimensional volume data is selected as reference data. However, a criterion for selecting reference data to acquire the target is not limited thereto. For example, the target acquisition unit 323 may select, from the three-dimensional volume data as reference data, B-scan data for which any one of an average value, a median, a maximum value, a mode, a variance, and a frequency width of luminance values is larger than a threshold. The threshold may be a predetermined threshold, or may be a threshold calculated from the three-dimensional volume data like the average value of all the luminances in the three-dimensional volume data in the third embodiment.

Similarly to the first embodiment, data to be corrected in the third embodiment is not limited to A-scan data, and as described above, the distribution of, for example, B-scan data or the entire three-dimensional volume data may be corrected to the target distribution.

Further, similarly to the first embodiment, the data correction unit 324 may correct only the distribution of a piece of A-scan data for which the statistical value of luminances contained in the A-scan data is smaller than a predetermined value from among pieces of A-scan data contained in the three-dimensional volume data. The statistical value may be, for example, a sum, an average value, a median, a maximum value, a variance, and a mode. Further, when the data to be corrected is, for example, the distribution of B-scan data, the data correction unit 324 can correct only the distribution of the data to be corrected for which the statistical value of luminances contained in the data to be corrected is smaller than a predetermined threshold, depending on units of the distribution of the data to be corrected.

Further, in the third embodiment, the target acquisition unit 323 calculates the average value of luminances of B-scan data for selection of the one serving as reference data to be used for calculating the target. However, the units of data for calculating the average value at the time of selection of reference data are not limited thereto. For example, the target acquisition unit 323 may calculate the average value for each piece of A-scan data or each piece of three-dimensional volume data to select reference data. Alternatively, the target acquisition unit 323 may calculate the average value for a plurality of consecutive pieces of A-scan data obtained by dividing B-scan data in a strip form or for a plurality of similar consecutive pieces of B-scan data. Further, the target acquisition unit 323 may calculate the average value of luminances of a plurality of pieces of three-dimensional volume data obtained by imaging the same range a plurality of times to select reference data. Also in those cases, the target acquisition unit 323 calculates the target based on the selected reference data.

Further, in the method of setting the target in the third embodiment, the target acquisition unit 323 acquires one target for tomographic data in the three-dimensional volume data. However, a separate target may be acquired for tomographic data of each specific range. For example, the target acquisition unit 323 may calculate the target based on a piece of A-scan data to be corrected, a group of one or more pieces of A-scan data adjacent to a piece of B-scan data, or a group of pieces of B-scan data. Similarly, the target may be calculated from a plurality of pieces of A-scan data to be corrected, a group of a plurality of pieces of A-scan data adjacent to B-scan data, or a group of a plurality of pieces of B-scan data. Examples in those cases are now described with reference to FIG. 10A to FIG. 10D. The width between scanning lines in FIG. 10A to FIG. 10D is wider than an actual width for the sake of description. In actuality, the width between adjacent scanning lines is extremely small, and thus the distribution of tomographic data between adjacent scanning lines or a group of scanning lines is essentially and substantially the same.

Figure 10A:
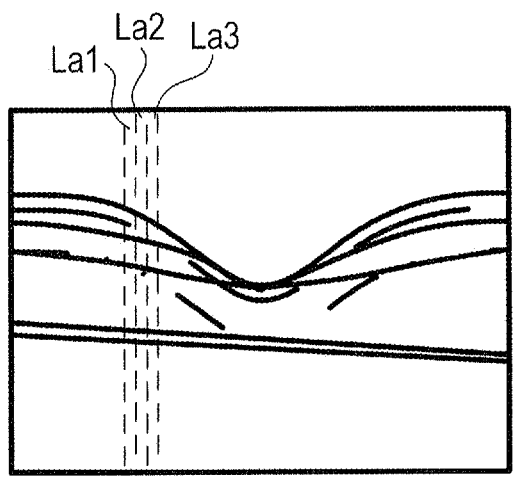
FIG. 10A is a diagram for illustrating correction of a data distribution in a modified example of the third embodiment.
Figure 10B:
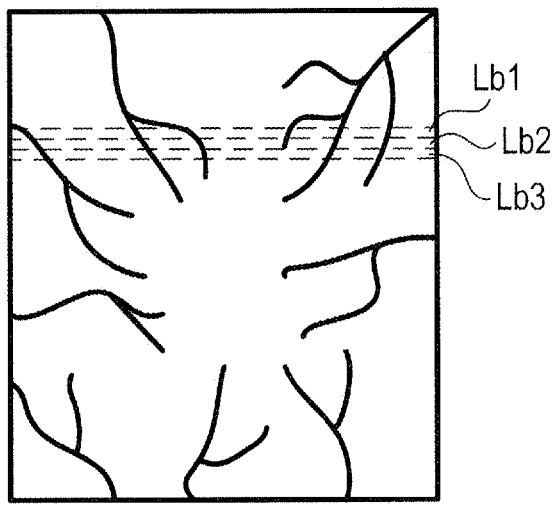
FIG. 10B is a diagram for illustrating correction of the data distribution in the modified example of the third embodiment.

FIG. 10A is an illustration of a case in which the target is calculated from a group of pieces of A-scan data adjacent to a piece of A-scan data to be corrected. In this case, the target acquisition unit 323 selects a group of pieces of A-scan data La1 and La3 adjacent to a piece of A-scan data La2 to be corrected as reference data. That is, the group of pieces of A-scan data La1 and La3, which are acquired from a group of A-scan lines adjacent to an A-scan line from which the A-scan data La2 is acquired, are selected as reference data. Then, the target average value and standard deviation are acquired from the group of pieces of A-scan data La1 and La3. The average value and standard deviation are acquired in a manner similar to the above-mentioned method. Similarly, FIG. 10B is an illustration of a case of acquiring the target from a group of pieces of B-scan data adjacent to a piece of B-scan data to be corrected. In this case, a group of pieces of B-scan data Lb1 and Lb3, which are acquired from a group of B-scan lines adjacent to a B-scan line from which B-scan data Lb2 is acquired, are selected as reference data. Then, the target average value and standard deviation are calculated from the group of pieces of B-scan data Lb1 and Lb3.

Figure 10C:
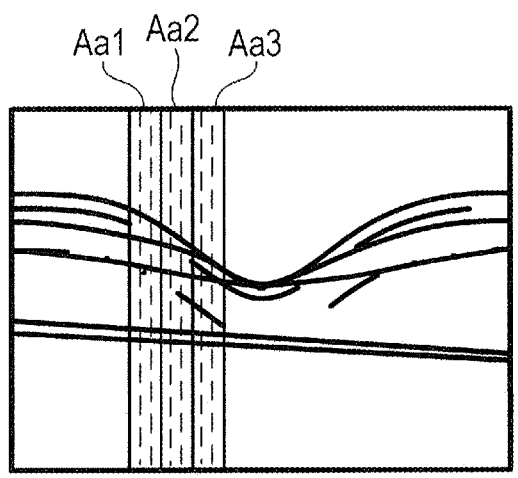
FIG. 10C is a diagram for illustrating correction of the data distribution in the modified example of the third embodiment.
Figure 10D:
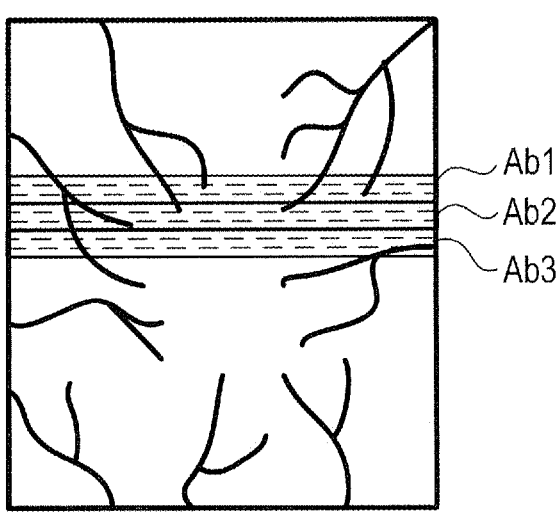
FIG. 10D is a diagram for illustrating correction of the data distribution in the modified example of the third embodiment.

Similarly, FIG. 10C is an illustration of a case in which the target is calculated from a group of a plurality of pieces of A-scan data adjacent to a plurality of pieces of A-scan data to be corrected. In this case, the target acquisition unit 323 selects a group of a plurality of pieces of A-scan data Aa1 and Aa3 adjacent to a plurality of pieces of A-scan data Aa2 to be corrected as reference data. That is, the group of pieces of A-scan data Aa1 and Aa3, which are acquired from areas that are adjacent to an area from which the plurality of pieces of A-scan data Aa2 are acquired and has sizes corresponding to that of the area, an A-scan line from which a plurality of the A-scan data Aa2 is acquired, are selected as reference data. Then, the target average value and standard deviation are acquired from the group of the plurality of pieces of A-scan data Aa1 and Aa3. Similarly, FIG. 10D is an illustration of a case in which the target is calculated from a group of a plurality of pieces of B-scan data adjacent to a plurality of pieces of B-scan data to be corrected. In this case, the target acquisition unit 323 selects a group of pieces of B-scan data Ab1 and Ab3, which are acquired from areas that are adjacent to an area from which a plurality of pieces of B-scan data Ab2 are acquired and has sizes corresponding to that of the area, as reference data. Then, the target average value and standard deviation are calculated from the group of pieces of Ab1 and Ab3 of the plurality of pieces of B-scan data.

In this manner, the target acquisition unit 323 can set the target based on pieces of tomographic data adjacent to a piece of tomographic data having the distribution of the parameter to be corrected. In this case, the data correction unit 324 can perform correction of parts of B-scan data containing, for example, a macular area and a papillary edge, for which the distributions of tomographic data are slightly different from those of tomographic data on other parts, in consideration of characteristics of those distributions of the macular area and the papillary edge. Therefore, the control unit can effectively correct a change in tomographic data in such a manner as to suit a more realistic condition.

In such cases, the data correction unit 324 compares the distributions of a group of pieces of tomographic data adjacent to a piece of tomographic data, which is potential data to be corrected, with the distribution of the piece of tomographic data, and only when a difference between statistical values of those distributions is larger than a predetermined threshold, the distribution of the relevant tomographic data may be corrected. As the difference between statistical values of distributions, for example, at least one difference may be taken from among average values, maximum values, modes, variances, or frequency widths in the distributions of pieces of tomographic data to be compared. In this case, the data correction unit 324 corrects only the tomographic data for which the distribution is different from those of the group of adjacent pieces of tomographic data by a certain degree or more. Therefore, it is possible to reduce the amount of calculation required for correction and shorten the processing time.

Further, similarly to the above-mentioned case, the target acquisition unit 323 may calculate the target from the group of one or more pieces of three-dimensional volume data for which the three-dimensional volume data to be corrected and the imaging time are temporally continuous.

Correction of the distribution of tomographic data in the third embodiment described above is not limited to correction of the distribution of tomographic data directly generated from an interference signal acquired by the imaging optical system 200. Other correction of tomographic data may involve, for example, correction of the distribution of tomographic data subjected to correction processing (hereinafter referred to as "roll-off correction") for compensating for signal attenuation in the depth direction due to roll-off characteristics of the imaging apparatus.

In the following, the roll-off correction processing is briefly described. A correction coefficient H(z) in the depth direction for performing roll-off correction is represented by, for example, Expression (11) when a normalization roll-off characteristic function RoF(z) has an argument of a depth position z.

$$R(z) = \frac{1}{1 + RoF(z) - RoF(z_0)} \quad \text{Expression (10)}$$

$$H(z) = \frac{(BGa + 2\sigma)}{BGa(z) + 2\sigma(z)} \times R(z) \quad \text{Expression (11)}$$

In Expression (11), BGa and σ represent the average value and standard deviation, which are statistical values relating to a luminance distribution BG of the entire B-scan data acquired under a state in which there is no object to be inspected, respectively. Further, BGa(z) and σ(z) represent the average value and standard deviation of a luminance distribution relating to a direction orthogonal to a Z-axis, which are calculated at the depth position (z) for the B-scan data acquired under the state in which there is no object to be inspected. Further, $z_0$ represents a reference depth position included in a B-scan range. The reference depth position $z_0$ may be set to any constant, but it is assumed that $z_0$ is set to ¼ of the maximum value of z. BGa and σ may represent the average value and standard deviation, which are statistical values relating to the luminance distribution BG of the entire A-scan data acquired a plurality of times under a state in which there is no object to be inspected, respectively.

Similarly, BGa(z) and σ(z) may represent the average value and standard deviation of a luminance distribution relating to a direction orthogonal to the Z-axis, which are calculated at the depth position (z) for the A-scan data acquired a plurality of times under the state in which there is no object to be inspected.

Figure 11A:
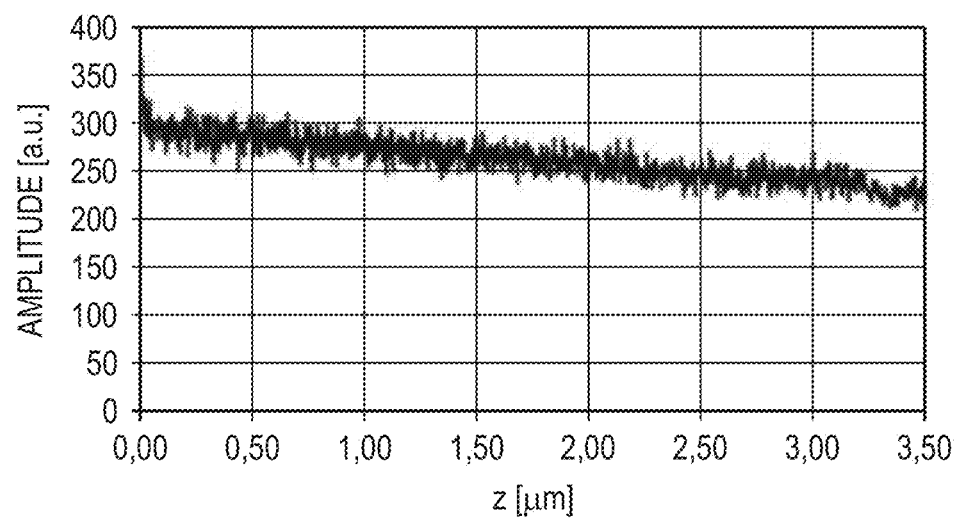
FIG. 11A is a graph for showing data distribution before application of processing of compensating for signal attenuation in a depth direction due to roll-off characteristics in fourth and fifth embodiments of this disclosure.
Figure 11B:
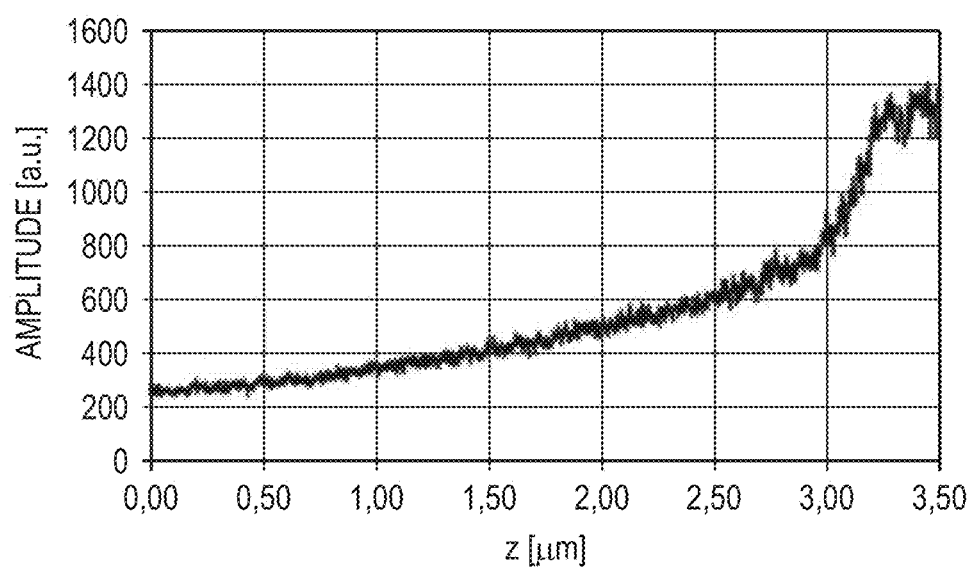
FIG. 11B is a graph for showing data distribution after application of the processing of compensating for signal attenuation in the depth direction due to the roll-off characteristics in the fourth and fifth embodiments.

FIG. 11A is a graph for showing an example of the average value BGa(z) of the luminance at each depth position (z) in the B-scan data acquired under the state in which there is no object to be inspected. Further, FIG. 11B is a graph for showing an example of a result of compensating for signal attenuation in the depth direction by multiplying the average value BGa(z) by the correction coefficient H(z). In FIG. 11A and FIG. 11B, the horizontal axis represents the depth position z, and the vertical axis represents an amplitude of complex number data corresponding to the luminance.

Three-dimensional volume data Ih(x, y, z) subjected to roll-off correction is represented by Expression (12) given below.

$$Ih(x,y,z)=Io(x,y,z) \times H(z) \quad \text{Expression (12)}$$

Such roll-off correction enables acquisition of tomographic data that has reduced signal attenuation in the depth direction due to roll-off characteristics of the imaging apparatus. The target acquisition unit 323 in the control unit 300 in the third embodiment acquires the correction coefficient H(z) based on the tomographic data acquired from the reconstruction unit 321. After that, the data correction unit 324 performs roll-off correction based on the correction coefficient H(z), and corrects the distribution of tomographic data subjected to roll-off correction in the third embodiment.

In this manner, correction of the distribution of tomographic data in the third embodiment may be performed in combination with other correction techniques, for example, roll-off correction, and a roll-off correction expression is not limited to the one described above, and any known correction expression may be used. Further, the parameter of tomographic data to be used for roll-off correction can be adopted in accordance with the parameter to be used for calculating a motion contrast.

Fourth Embodiment

In the third embodiment, the target (average value and standard deviation) of the distribution of a parameter is calculated from the three-dimensional volume data generated by the reconstruction unit 321, and corrects the distribution of the parameter of tomographic data so that the distribution becomes closer to the target. In contrast, in a fourth embodiment of this disclosure, the approximate value of tomographic data that is projected in the front direction of the fundus is calculated based on the three-dimensional volume data to obtain a correction coefficient, and the parameter of tomographic data is corrected based on the acquired correction coefficient.

Imaging of a tomographic image by OCT takes a longer period of time from initial scanning to re-scanning due to causes such as an order of scanning or a failure to fix eyes, and during that period, states (e.g., positions of eyelids, eyelashes, and pupils) of the eye to be inspected may change. In this case, the signal strength of an interference signal to be acquired changes depending on, for example, a change in imaging condition, and deviation of pixel values in the tomographic image generated based on the interference signal occurs. When tomographic data that is based on such an interference signal is used, a tomographic image or motion contrast data containing a low-luminance area due to deviation of pixel values is generated to hinder observation or analyzation.

In view of the above, in the fourth embodiment, a correction coefficient of tomographic data is calculated based on the distribution of approximate values of tomographic data, and the parameter of the tomographic data is corrected using the correction coefficient, to thereby obtain a high-definition OCTA image without being influenced by partial contrast of the tomographic image.

More specifically, in the fourth embodiment, as a first approximate parameter, a parameter of tomographic data obtained by smoothing, in the two-dimensional direction, a projection image of the front of the fundus that is based on the three-dimensional volume data is acquired. Further, as a second parameter, a parameter of tomographic data obtained by smoothing the projection image in a one-dimensional direction (main-scanning axis direction) is acquired. After that, the first approximate parameter is divided by a second approximate parameter to calculate a correction coefficient. The calculated correction coefficient is used to correct the parameter of tomographic data, and the corrected parameter of tomographic data is used to calculate a motion contrast. With this, tomographic data corresponding to a low luminance area is corrected with a correction coefficient that is based on the approximate parameter, and thus it is possible to obtain a high-definition OCTA image without being influenced by partial contrast of the tomographic image.

In the following, with reference to FIG. 12 to FIG. 14C, the control unit in the fourth embodiment is described. Components of the control unit in the fourth embodiment are similar to components of the control unit 300 in the third embodiment, and thus the same reference numerals are used to omit descriptions thereof. In the following, the control unit in the fourth embodiment is described with emphasis on a difference from the control unit 300 in the third embodiment.

Figure 12:
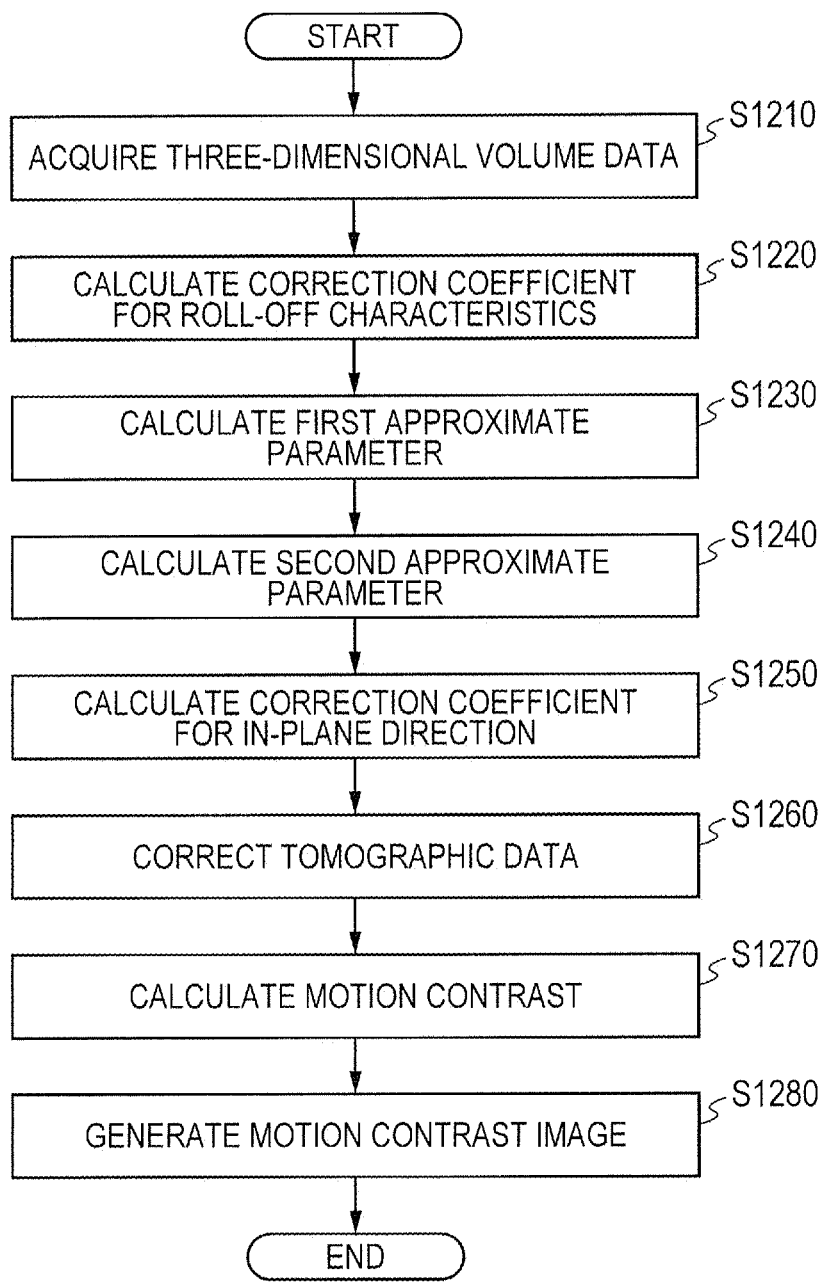
FIG. 12 is an illustration of a flow of OCTA image generation processing in the fourth embodiment.

FIG. 12 is a flowchart for illustrating OCTA image generation processing in the fourth embodiment. Step S1210, Step S1270, and Step S1280 in the flowchart illustrated in FIG. 12 are similar to those of the OCTA image generation processing in the third embodiment, and thus a description thereof is omitted here.

Figure 13A:
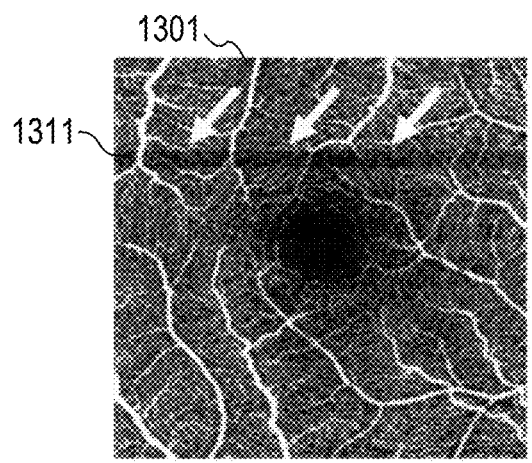
FIG. 13A is an image for showing the OCTA image generation processing in the fourth embodiment.
Figure 13B:
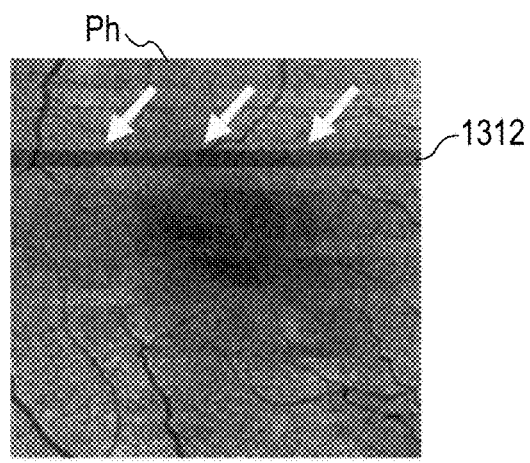
FIG. 13B is an image for showing the OCTA image generation processing in the fourth embodiment.
Figure 13C:
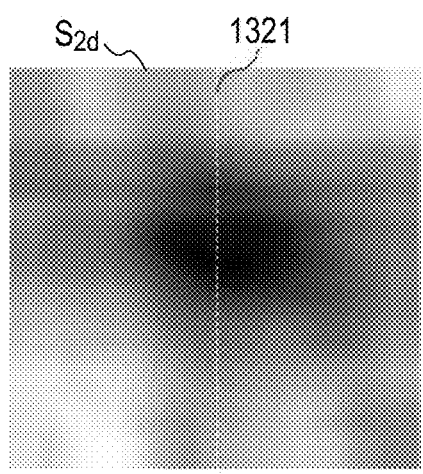
FIG. 13C is an image for showing the OCTA image generation processing in the fourth embodiment.
Figure 13D:
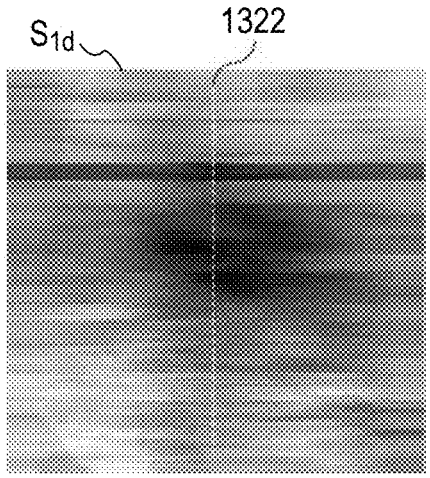
FIG. 13D is an image for showing the OCTA image generation processing in the fourth embodiment.
Figure 13E:
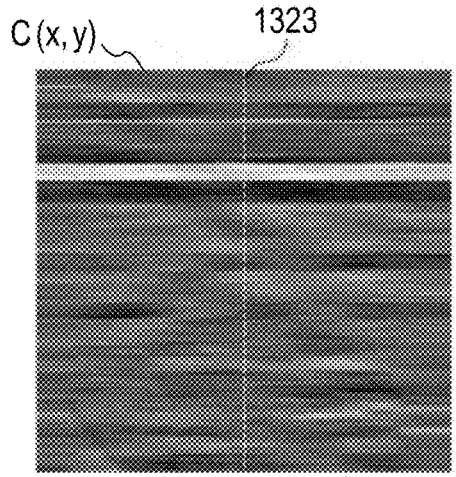
FIG. 13E is an image for showing the OCTA image generation processing in the fourth embodiment.
Figure 13F:
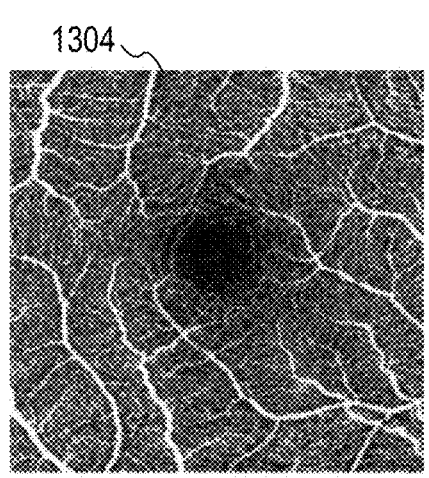
FIG. 13F is an image for showing the OCTA image generation processing in the fourth embodiment.

FIG. 13A to FIG. 13F are images for showing examples of an OCTA image, a projection image, and the like relating to the OCTA image generation processing in the fourth embodiment. It is assumed that the images shown in FIG. 13A to FIG. 13F are generated based on the same three-dimensional volume data. FIG. 13A is an image for showing an OCTA image 1301 that is generated without application of the processing in the fourth embodiment. FIG. 13B is an image for showing an OCT projection image Ph corresponding to the front of the fundus. FIG. 13C represents a first approximate parameter $S_{2d}(x, y)$ obtained by smoothing the OCT projection image Ph in the two-dimensional direction. FIG. 13D represents a second approximate parameter $S_{1d}(x, y)$ obtained by smoothing the OCT projection image Ph in the one-dimensional direction (main scanning direction). FIG. 13E represents a correction coefficient $C(x, y)$ obtained by dividing the first approximate parameter $S_{2d}(x, y)$ by the second approximate parameter $S_{1d}(x, y)$. FIG. 13F represents an OCTA image 1304 generated by the OCTA image generation processing in the fourth embodiment. The values (x, y) herein indicate each pixel position on an xy plane corresponding to the front of the fundus.

With reference to FIG. 13B, as indicated by the white arrows, a low luminance area 1312 exists in the OCT projection image Ph, and a difference in luminance occurs in the sub-scanning direction (vertical direction). Usage of such tomographic data containing the low luminance area 1312 causes generation of an OCTA image 1301 including a low luminance area 1311 as indicated by the white arrows of FIG. 13A to hinder observation or analyzation. Thus, in the fourth embodiment, approximate parameters obtained by calculating an approximate parameter distribution of tomographic data are used to calculate a correction coefficient, and the correction coefficient is used to correct tomographic data, to thereby reduce occurrence of a low-luminance area. The approximate value distribution of tomographic data refers to tomographic data obtained by smoothing tomographic data or transforming tomographic data by morphology calculation described later, and for example, corresponds to approximate parameters shown in FIG. 13C and FIG. 13D.

First, in Step S1210, the acquisition unit 310 acquires three-dimensional volume data, and then the processing advances to Step S1220. In Step S1220, the target acquisition unit 323 calculates the correction coefficient H(z) in the depth direction for roll-off correction by the above-mentioned technique in order to compensate for signal attenuation due to roll-off characteristics of the OCT apparatus 1.

Next, in Step S1230, the target acquisition unit 323 smooths the projection image of the front of the fundus that is based on three-dimensional volume data in the two-dimensional direction, to thereby calculate the first approximate parameter. Specifically, the target acquisition unit 323 projects the three-dimensional volume data Ih(x, y, z) subjected to roll-off correction in the depth direction, and generates the OCT projection image Ph corresponding to the front of the fundus as shown in FIG. 13B. The target acquisition unit 323 smoothes the generated OCT projection image Ph in the two-dimensional direction for each pixel, to thereby calculate the first approximate parameter $S_{2d}(x, y)$ of the parameter of tomographic data as shown in FIG. 13C.

In the fourth embodiment, as the processing of projecting three-dimensional volume data, the average value of luminances of tomographic data in the depth direction, which corresponds to pixels on a plane corresponding to the front of the fundus, is set as a pixel value of the pixel. However, the projection processing is not limited to such average value projection, and any known projection method may be used. For example, a median, a maximum value, a mode or such values of pieces of tomographic data in the depth direction corresponding to respective pixels may be set as the pixel value. Further, a pixel value (due to luminance value of fundus structure) having excluded influences of the background area can be acquired by projecting only the pixel value of a pixel that has exceeded a noise threshold corresponding to a background luminance value. Further, in the fourth embodiment, smoothing processing is performed as an example of processing of calculating an approximate value distribution. However, as described later, morphology calculation such as closing processing or opening processing may be performed. Further, smoothing processing may be performed using any spatial filter, or may be performed by transforming frequencies of tomographic data using fast Fourier transform (FFT) or other techniques and suppressing high-frequency components. When FFT is used, convolution calculation is not required, and thus it is possible to execute the smoothing processing at a high speed.

In Step S1240, the target acquisition unit 323 performs processing (smoothing processing or morphology calculation) of calculating an approximate value distribution relating to the main scanning direction (one-dimensional direction) of measurement light for each pixel of the OCT projection image Ph, to thereby calculate the second approximate parameter $S_{1d}(x, y)$. After that, in Step S1250, the target acquisition unit 323 divides the first approximate parameter $S_{2d}(x, y)$ by the second approximate parameter $S_{1d}(x, y)$ in accordance with Expression (13), to thereby calculate the correction coefficient C(x, y) as shown by FIG. 13C.

$$C(x,y)=S_{2d}(x,y)/S_{1d}(x,y) \qquad \text{Expression (13)}$$

Figure 14A:
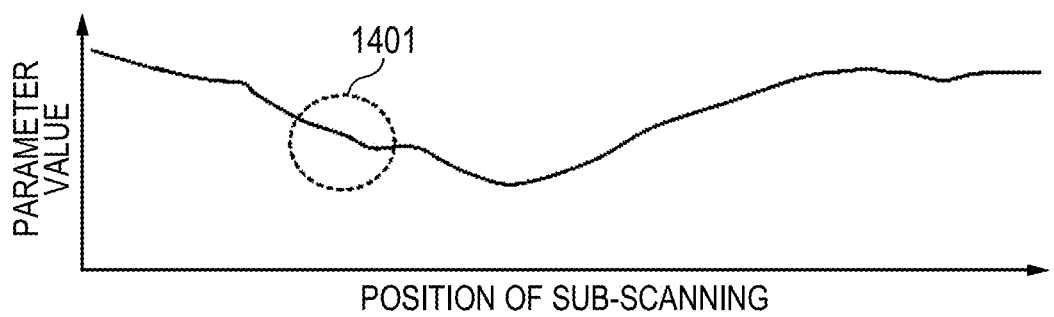
FIG. 14A is a graph for showing a luminance profile corresponding to the white dotted line of the image shown in FIG. 13C.
Figure 14B:
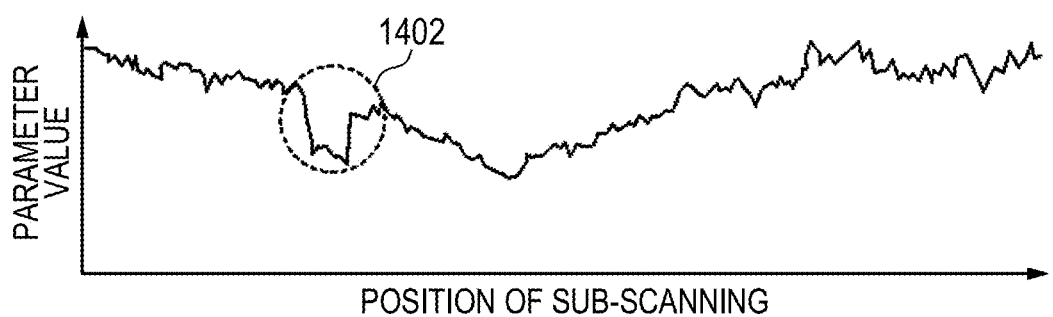
FIG. 14B is a graph for showing a luminance profile corresponding to the white dotted line of the image shown in FIG. 13D.
Figure 14C:
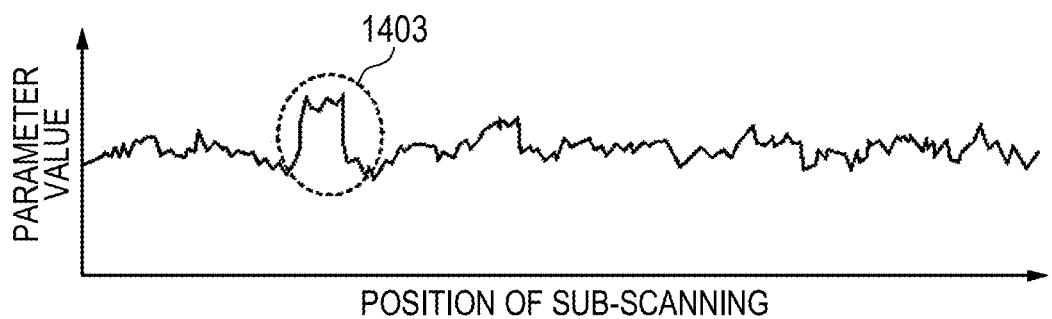
FIG. 14C is a graph for showing a luminance profile corresponding to the white dotted line of the image shown in FIG. 13E.

FIG. 14A, FIG. 14B, and FIG. 14C are graphs for showing profiles of the parameter of tomographic data that follow white dotted lines 1321, 1322, and 1323 drawn in the sub-scanning direction (vertical direction) in FIG. 13C, FIG. 13D, and FIG. 13E, respectively. In FIG. 14A to FIG. 14C, the profiles of positions corresponding to the low luminance area 1312 of the OCT projection image Ph are represented by circles 1401, 1402, and 1403. The target acquisition unit 323 performs the processing described above to determine the correction coefficient C(x, y) so that the profile of the position corresponding to the low luminance area 1312 of the OCT projection image Ph enclosed by the circle 1402 becomes closer to the profile of the first approximate parameter $S_{2d}(x, y)$ enclosed by the circle 1401. The circle 1403 represents the profile of the correction coefficient C(x, y) at the position corresponding to the low luminance area 1312.

In Step S1260, the data correction unit 324 uses the correction coefficient H(z) in the depth direction determined in Step S1220 and the correction coefficient C(x, y) in the in-plane direction calculated in Step S1250 to correct the parameter of tomographic data. Specifically, the data correction unit 324 corrects the parameter of tomographic data in accordance with Expression (14), where the original three-dimensional volume data (tomographic data) represents Io(x, y, z) and the corrected tomographic data represents Ic(x, y, z).

$$Ic(x,y,z)=Io(x,y,z) \times H(z) \times C(x,y) \qquad \text{Expresssion (14)}$$

The following processing is similar to that of the third embodiment, and thus a description thereof is omitted here. According to the OCTA image generation processing in the fourth embodiment, it is possible to generate an OCTA image, which is a motion contrast image that has suppressed occurrence of contrast due to deviation of tomographic data as shown in FIG. 13F.

As described above, the control unit 300 in the fourth embodiment includes the acquisition unit 310, the target acquisition unit 323, the data correction unit 324, and the image generation unit 320. The acquisition unit 310 acquires a plurality of pieces of tomographic data each representing information on a cross section of the fundus, which is acquired based on the measurement light controlled to scan the same position of the fundus of the eye to be inspected E. The target acquisition unit 323 calculates the first approximate parameter obtained by smoothing in the first dimension or performing morphology calculation of the parameter to be used for calculating a motion contrast in tomographic data. Further, the target acquisition unit 323 calculates the second approximate parameter obtained by smoothing in the second dimension smaller than the first dimension or performing morphology calculation of the parameter of tomographic data. After that, the target acquisition unit 323 performs an arithmetic operation on the first approximate parameter and the second approximate parameter to obtain the correction coefficient. In the fourth embodiment, the luminance of tomographic data is used as the parameter. The data correction unit 324 uses the correction coefficient to correct the parameter of at least one piece of tomographic data among a plurality of pieces of tomographic data. The image generation unit 320 generates a motion contrast image based on motion contrast calculated using the plurality of pieces of tomographic data containing the at least one tomographic data corrected by the data correction unit 324.

More specifically, the target acquisition unit 323 calculates the first approximate parameter by smoothing in the two-dimensional direction or transforming by morphology calculation the parameter of tomographic data corresponding to the front of the fundus. Further, the target acquisition unit 323 calculates the second approximate parameter by smoothing (in the first-dimensional direction) in the main scanning direction of measurement light or transforming by morphology calculation the parameter of tomographic data corresponding to the front of the fundus. After that, the target acquisition unit 323 divides the first approximate parameter by the second approximate parameter to calculate the correction coefficient.

When the parameter of tomographic data is smoothed or subjected to morphology calculation, parameters between adjacent pieces of tomographic data can be transformed to have a decreased difference in value. Thus, through the configuration described above, the target acquisition unit 323 can calculate a first transformed parameter that has transformed parameters adjacent in the first direction and second direction in tomographic data to have a decreased difference in value. Further, the target acquisition unit 323 can calculate a second transformed parameter that has transformed parameters adjacent in the first direction in tomographic data to have a decreased difference in value. After that, the target acquisition unit 323 divides the first transformed parameter acquired as the first approximate parameter by the second transformed parameter acquired as the second approximate parameter, to thereby acquire the correction coefficient.

According to the control unit 300 in the fourth embodiment, parameters of tomographic data serving as original data for generating a motion contrast are corrected based on the approximate value distribution of those parameters. Thus, contrast due to each parameter is suppressed. Therefore, it is possible to generate an OCTA image, which is a motion contrast image that has suppressed occurrence in contrast due to deviation of tomographic data.

Further, in the fourth embodiment, the target acquisition unit 323 acquires a correction coefficient using tomographic data subjected to roll-off correction processing for compensating for signal attenuation in the depth direction due to roll-off characteristics of the imaging optical system 200 configured to image the fundus. Thus, it is possible to generate an OCTA image, which is a motion contrast image that has reduced influences of signal attenuation in the depth direction due to roll-off characteristics of the imaging optical system 200.

In the fourth embodiment, a description has been given of a case of only calculating the correction coefficient H(z) in the depth direction in Step S1220, and correcting the three-dimensional volume data Io(x, y, z) in accordance with Expression (14) in Step S1260. However, the timing of roll-off correction is not limited thereto. For example, the three-dimensional volume data Ih(x, y, z) that has performed roll-off correction in accordance with Expression (12) in Step S1220 may be generated in advance, and the three-dimensional volume data Ih(x, y, z) may be corrected in accordance with Expression (15) in Step S1250.

$$Ic(x,y,z) = Ih(x,y,z) \times C(x,y) \qquad \text{Expression (15)}$$

Further, in the fourth embodiment, roll-off correction is performed together with correction for reducing a low-luminance area. However, the roll-off correction may not be performed. In this case, Step S1220 is omitted, and in Step S1260, the correction coefficient H(z) in the depth direction is omitted. Further, in Step S1230 and Step S1240, the first approximate parameter and the second approximate parameter are calculated based on the three-dimensional volume data that has not been subjected to roll-off correction.

Further, in the fourth embodiment, the OCT projection image Ph is generated, and the correction coefficient C(x, y) is generated as a two-dimensional coefficient, but this disclosure is not limited thereto. For example, the approximate value distribution of the parameter of tomographic data obtained by smoothing three-dimensional volume data three-dimensionally may be set as the first approximate parameter. In this case, the approximate value distribution of the parameter of tomographic data obtained by smoothing the tomographic data in the two-dimensional direction of the x-axis direction and the depth (z-axis) direction is set as the second approximate parameter so that correction effects for contrast (luminance difference in y-axis direction) in luminance to be corrected are improved. After that, the three-dimensional correction coefficient may be generated based on a value obtained by dividing the first approximate parameter by the second approximate parameter to correct the tomographic data.

In the fourth embodiment, the smoothing processing is performed as an example of processing of calculating the approximate value distribution. However, the processing of calculating the approximate value distribution is not limited thereto. The approximate value distribution calculation processing herein includes, for example, any known approximate value distribution calculation processing such as smoothing processing or morphology processing using FFT. For example, closing processing (processing of executing minimum value calculation after maximum value calculation), which is a type of morphology calculation, may be performed instead of smoothing processing, and the parameter subjected to morphology processing may be set as the approximate parameter. For example, when the width of a low luminance area is wide, it is possible to prevent the approximate parameter from being set extremely low by setting the approximate parameter based on the closing processing. Further, the processing of calculating the approximate parameter distribution may be performed in combination with, for example, the smoothing processing or morphology calculation.

Further, in the fourth embodiment, a variation pattern of the parameter to be corrected has been described taking the case of contrast in luminance, which occurs only in the sub-scanning direction, as an example. However, the variation pattern of the parameter to be corrected is not limited thereto. When the variation pattern indicates a smaller local change of the first approximate parameter, the variation pattern that occurs at any position or in any direction can be corrected. In this case, the position or direction for performing smoothing or morphology calculation at the time of calculating the second approximate parameter can be changed depending on the variation pattern to be corrected, to thereby correct the variation pattern of a parameter at any position or in any direction.

Further, in the fourth embodiment, the first approximate parameter $S_{2d}(x, y)$ is divided by the second approximate parameter $S_{1d}(x, y)$ as calculation for obtaining the correction coefficient C(x, y). However, the calculation is not limited to division, and any calculation may be performed. For example, subtraction processing may be performed as the calculation processing.

In the fourth embodiment, the configuration for correcting tomographic data over the entire three-dimensional volume data has been described, but the correction processing is not limited thereto. For example, only the tomographic data contained in the range of generation of an OCTA image, which is a motion contrast image to be generated, may be corrected. In this case, only the tomographic data contained in the range of generation of an OCTA image may be used for calculation of a correction coefficient. Thus, only the tomographic data contained in the range of generation of the OCTA image can be used at the time of generation of an OCT projection image. In such a case, the number of pieces of data to be used for calculation is decreased, and thus it is possible to reduce the calculation amount.

Fifth Embodiment

In the fourth embodiment, a description has been given of the case of correcting the parameter of tomographic data using the correction coefficient of the tomographic data calculated by using two types of approximate parameters of three-dimensional volume data. In contrast, in a fifth embodiment of this disclosure, a description is given of a case of generating a motion contrast image that has suppressed occurrence in contrast due to deviation of tomographic data by correcting a threshold to be applied to tomographic data at the time of calculation of a motion contrast using a similar correction coefficient. Specifically, similarly to the fourth embodiment, after the correction coefficient C(x, y) is calculated, the noise threshold Dth to be used for calculating a motion contrast is divided by the correction coefficient C(x, y) to correct the noise threshold Dth. After that, the obtained new noise threshold is used to calculate a motion contrast and generate a motion contrast image.

Figure 15:
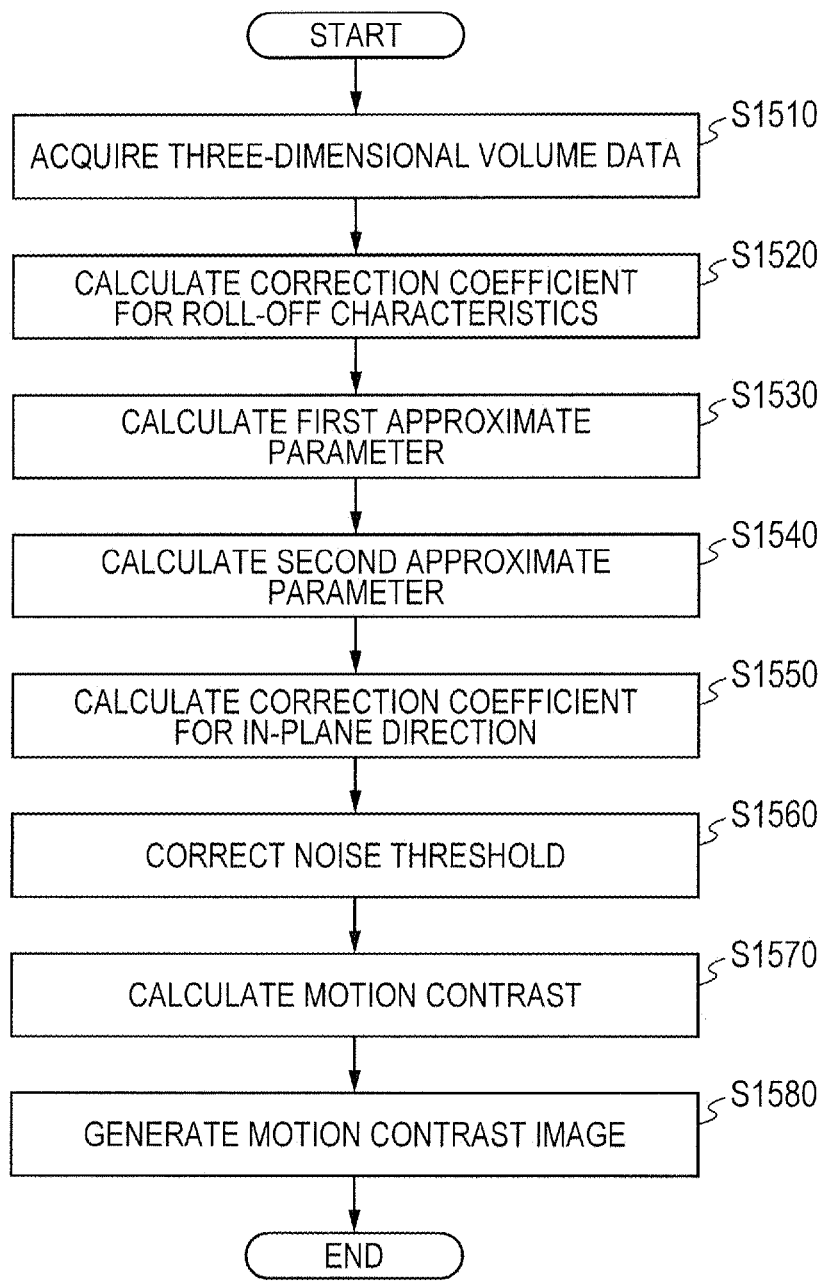
FIG. 15 is an illustration of a flow of OCTA image generation processing in a fifth embodiment of this disclosure.

In the following, with reference to FIG. 15, the control unit in the fifth embodiment is described with emphasis on a difference from the control unit 300 in the fourth embodiment. FIG. 15 is a flowchart for illustrating OCTA image generation processing in the fifth embodiment. In the flowchart illustrated in FIG. 15, steps other than Step S1560 and Step S1570 are similar to those of the OCTA image generation processing in the fourth embodiment, and thus a description thereof is omitted here.

In the fifth embodiment, in Step S1550, when the correction coefficient C(x, y) is calculated, the processing advances to Step S1560. In Step S1560, the motion contrast generation unit 325 uses the correction coefficient H(z) for roll-off correction and the correction coefficient C(x, y) in the in-plane direction to correct the noise threshold Dth for noise mask processing to be used for calculating a motion contrast. Specifically, the motion contrast generation unit 325 corrects the noise threshold Dth in accordance with Expression (16), to thereby calculate a noise threshold Dthc.

$$Dthc = \frac{Dth}{C(x, y) \times H(z)} \qquad \text{Expression (16)}$$

The corrected noise threshold Dthc becomes smaller as the parameter of tomographic data becomes smaller, that is, as the correction coefficient C(x, y) becomes larger and the depth position z becomes larger.

In Step S1560, the motion contrast generation unit 325 conducts noise mask processing on three-dimensional volume data Io (tomographic data) using the noise threshold Dthc. After that, the motion contrast generation unit 325 uses the three-dimensional volume data that has been subjected to the noise mask processing to calculate motion contrast and generate motion contrast data.

The subsequent processing is similar to that of the fourth embodiment and other embodiments, and thus a description thereof is omitted here. According to the OCTA image generation processing in the fifth embodiment too, it is possible to generate an OCTA image, which is a motion contrast image that has suppressed occurrence of contrast due to deviation of tomographic data.

As described above, the control unit 300 in the fifth embodiment includes the acquisition unit 310, the target acquisition unit 323, the data correction unit 324, and the image generation unit 320. The acquisition unit 310 acquires a plurality of pieces of tomographic data each representing information on a cross section of the fundus, which is acquired based on the measurement light controlled to scan the same position of the fundus of the eye to be inspected E. The target acquisition unit 323 calculates the first approximate parameter obtained by smoothing in the first dimension or performing morphology calculation of the parameter to be used for calculating a motion contrast in tomographic data. Further, the target acquisition unit 323 calculates the second approximate parameter obtained by smoothing in the second dimension smaller than the first dimension or performing morphology calculation of the parameter of tomographic data. After that, the target acquisition unit 323 performs an arithmetic operation on the first approximate parameter and the second approximate parameter to obtain the correction coefficient. In the fifth embodiment, the luminance of tomographic data is used as the parameter. The data correction unit 324 uses the correction coefficient to correct the threshold of threshold processing to be applied to the parameter of tomographic data. The image generation unit 320 generates a motion contrast image based on motion contrast calculated using the parameter of at least one piece of tomographic data among a plurality of pieces of tomographic data, which has been subjected to the threshold processing using the threshold corrected by the data correction unit 324.

According to the control unit 300 in the fifth embodiment, the noise threshold to be used for calculating a motion contrast is corrected based on the approximate parameter obtained by smoothing or performing morphology calculation of tomographic data, to thereby be able to reduce the possibility of a valid signal being subjected to threshold processing. Thus, it is possible to generate an OCTA image, which is a motion contrast image that has suppressed occurrence in contrast due to deviation of tomographic data.

In the fifth embodiment, a description has been given of a case of only calculating the correction coefficient H(z) in the depth direction in Step S1520, and correcting the noise threshold Dth to be applied to the three-dimensional volume data Io(x, y, z) in accordance with Expression (16) in Step S1560. However, data to be subjected to roll-off correction is not limited to the noise threshold Dth, and the roll-off correction may be applied to the three-dimensional volume data Io(x, y, z). For example, the three-dimensional volume data Ih(x, y, z) subjected to roll-off correction using Expression (12) is generated in advance in Step S1520, and the noise threshold Dth is corrected in accordance with Expression (17) given below in Step S1560. After that, in Step S1570, a corrected noise threshold Dthc' may be applied to the three-dimensional volume data Ih(x, y, z) subjected to roll-off correction. The corrected noise threshold Dthc' becomes smaller as the parameter of tomographic data becomes smaller, that is, the correction coefficient C(x, y) becomes larger.

$$Dthc' = \frac{Dth}{C(x, y)} \qquad \text{Expression (17)}$$

Further, in the fifth embodiment, roll-off correction is performed together with correction for reducing the low luminance area, but the roll-off correction may not be performed. In this case, Step S1520 is omitted, and the correction coefficient H(z) in the depth direction is omitted in correction of the noise threshold Dth in Step S1560. Further, in Step S1530 and Step S1540, the first approximate parameter and the second approximate parameter are calculated based on three-dimensional volume data that has not been subjected to roll-off correction.

In the fifth embodiment, a configuration for calculating the correction coefficient over the entire three-dimensional volume data has been described, but the method of calculating the correction coefficient is not limited thereto. For example, the correction coefficient may be calculated using only the tomographic data contained in the range of generation of an OCTA image, which is a motion contrast image to be generated. In this case, only the tomographic data contained in the range of generation of the OCTA image can be used also at the time of generation of an OCT projection image. In such a case, the number of pieces of data to be used for calculation is decreased, and thus it is possible to reduce the calculation amount.

According to the first to fifth embodiments described above, it is possible to generate a motion contrast image that has suppressed occurrence in contrast due to deviation of tomographic data.

Correction of data in the first to fifth embodiments described above can be conducted for each of three-dimensional volume data, B-scan data, A-scan data, or a part thereof depending on the desired configuration. Further, separate correction coefficients may be calculated for, for example, a plurality of pieces of three-dimensional volume data, or a common correction coefficient may be calculated.

In the first to fifth embodiments described above, the luminance (power) as complex number data subjected to FFT contained in the three-dimensional volume data is used as the parameter of tomographic data to generate motion contrast data. However, the motion contrast generation unit 325 may generate motion contrast data based on any known technique as the parameter such as phase information of complex number data subjected to FFT, information on both of the luminance and phase, or information on a real part and an imaginary part. In those cases, the data correction unit 324 corrects the distribution of information, for example, phase information to be used for generating motion contrast data, the information itself, or the noise threshold. After that, the motion contrast generation unit 325 generates motion contrast data based on the corrected information and noise threshold. With this, it is possible to exhibit effects similar to those of the embodiments described above.

Further, the data correction unit 324 may correct the distribution of tomographic data before being subjected to wavenumber transform, FFT, and absolute value transform, the tomographic data, or the noise threshold. Even in this case, the motion contrast generation unit 325 can exhibit effects similar to those of the embodiments described above by generating the motion contrast data based on, for example, the luminance of corrected tomographic data or noise threshold. In those cases, the target acquisition unit 323 acquires the target that depends on data to be corrected.

Further, in the first to fifth embodiments described above, motion contrast data is generated by acquiring the decorrelation value Mxy of two pieces of three-dimensional volume data at the time of generation of motion contrast data. However, the method of generating motion contrast data is not limited thereto. For example, the motion contrast generation unit 325 can generate motion contrast data by any known method, for example, a method of acquiring a difference or ratio of two pieces of three-dimensional volume data. The method of calculating the decorrelation value Mxy is not limited to Expression (1), and any known expression may be used.

Further, in the first to fifth embodiments described above, the acquisition unit 310 acquires an interference signal acquired by the imaging optical system 200, tomographic data generated by the image generation unit 320, and three-dimensional volume data generated by the reconstruction unit 321. However, the configuration for acquiring those signals by the acquisition unit 310 is not limited thereto. For example, the acquisition unit 310 may acquire those signals from a server or an imaging apparatus connected to the control unit via a LAN, WAN, or the Internet.

The eye to be inspected is taken as an example of the object to be inspected. However, the object to be inspected is not limited thereto. For example, the object to be inspected may be, for example, a skin or an organ of the subject. In this case, the OCT apparatus in the embodiments described above may be applied to a medical apparatus, for example, an endoscope.

Further, in the first to fifth embodiments described above, an optical fiber system to be used as a coupler as a division unit is used. However, a spatial optical system using a collimator or a beam splitter may be used. Further, the configuration of the imaging optical system 200 is not limited to the configuration described above, and a part of the configuration of the imaging optical system 200 may be configured as a component separate from the imaging optical system 200.

Further, in the first to fifth embodiments described above, the configuration of a Michelson interferometer is used as an interference optical system of the OCT apparatus. However, the configuration of the interference optical system is not limited thereto. For example, the interference optical system of the OCT apparatus 1 may have the configuration of a Mach-Zehnder interferometer.

Further, while the spectral-domain OCT (SD-OCT) apparatus, which uses the SLD as the light source, is described as the OCT apparatus in the first to fifth embodiments, the configuration of the OCT apparatus according to this disclosure is not limited thereto. For example, this disclosure is also applicable to a swept-source OCT (SS-OCT) apparatus, which uses a wavelength-swept light source capable of sweeping a wavelength of emitted light, or other such freely-selected type of OCT apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-052761, filed Mar. 17, 2017, and Japanese Patent Application No. 2017-171831, filed Sep. 7, 2017 which are hereby incorporated by reference herein in their entirety.

What is claimed is:

1. An information processing apparatus comprising:
at least one of (a) one or more processors and (b) circuitry, configured to function as a plurality of units comprising:
(1) a first acquisition unit configured to acquire a plurality of pieces of tomographic data each representing information on a cross section of a fundus, which is acquired based on measurement light controlled to scan the same position of the fundus;
(2) a second acquisition unit configured to acquire a correction coefficient by performing an arithmetic operation on (a) a first approximate parameter, which is obtained by transforming, in a first dimension, a parameter of a piece of tomographic data to be used for calculating a motion contrast, and (b) a second approximate parameter, which is obtained by transforming the parameter of the piece of tomographic data in a second dimension smaller than the first dimension;
(3) a correction unit configured to correct at least one piece of tomographic data among the plurality of pieces of tomographic data using the correction coefficient; and
(4) a generation unit configured to generate a motion contrast image based on a motion contrast calculated using the plurality of pieces of tomographic data including the corrected at least one piece of tomographic data.

2. An information processing apparatus according to claim 1, wherein the second acquisition unit is configured to:
calculate the first approximate parameter by transforming, in a two-dimensional direction, the parameter of a piece of tomographic data corresponding to a front of the fundus; and
calculate the second approximate parameter by transforming, in a one-dimensional direction, the parameter of the piece of tomographic data corresponding to the front of the fundus.

3. An information processing apparatus according to claim 2, wherein the one-dimensional direction includes an axial direction of main scanning by the measurement light.

4. An information processing apparatus according to claim 1, wherein the arithmetic operation includes an operation of dividing the first approximate parameter by the second approximate parameter.

5. An information processing apparatus according to claim 1, wherein the second acquisition unit is configured to acquire the correction coefficient using a piece of tomographic data subjected to roll-off correction processing for compensating for signal attenuation in a depth direction that is based on roll-off characteristics of an imaging apparatus configured to image the fundus.

6. An information processing apparatus comprising:
at least one of (a) one or more processors and (b) circuitry, configured to function as a plurality of units comprising:
(1) a first acquisition unit configured to acquire a plurality of pieces of tomographic data each representing information on a cross section of a fundus, which is acquired based on measurement light controlled to scan the same position of the fundus;
(2) a second acquisition unit configured to acquire a correction coefficient by performing an arithmetic operation on (a) a first approximate parameter, which is obtained by transforming, in a first dimension, a parameter of a piece of tomographic data to be used for calculating a motion contrast, and (b) a second approximate parameter, which is obtained by transforming the parameter of the piece of tomographic data in a second dimension smaller than the first dimension;
(3) a correction unit configured to correct a threshold of threshold processing to be applied to the parameter of the piece of tomographic data using the correction coefficient; and
(4) a generation unit configured to generate a motion contrast image based on a motion contrast calculated using a parameter of at least one piece of tomographic data among the plurality of pieces of tomographic data, which has been subjected to the threshold processing using the corrected threshold.

7. An information processing apparatus according to claim 6, wherein the second acquisition unit is configured to acquire the correction coefficient using a piece of tomographic data subjected to roll-off correction processing for compensating for signal attenuation in a depth direction that is based on roll-off characteristics of an imaging apparatus configured to image the fundus.

8. An information processing apparatus comprising:
at least one of (a) one or more processors and (b) circuitry, configured to function as a plurality of units comprising:
(1) a first acquisition unit configured to acquire a plurality of pieces of tomographic data each representing information on a cross section of a fundus, which is acquired based on measurement light controlled to scan the same position of the fundus;
(2) a second acquisition unit configured to acquire a correction coefficient by performing an arithmetic operation on (a) a first transformed parameter, which is obtained by transforming a parameter of a piece of tomographic data to be used for calculating a motion contrast so that a difference in value between parameters adjacent in a first direction and a second direction is decreased, and (b) a second transformed parameter, which is obtained by transforming the parameter of the piece of tomographic data so that a difference in value between parameters adjacent in the first direction is decreased;
(3) a correction unit configured to correct at least one piece of tomographic data among the pieces of tomographic data using the correction coefficient; and
(4) a generation unit configured to generate a motion contrast image based on a motion contrast calculated using the plurality of pieces of tomographic data including the corrected at least one piece of tomographic data.

9. An information processing apparatus according to claim 1, wherein the transformation includes one of smoothing and performing morphology calculation.

10. An information processing apparatus comprising:
at least one of (a) one or more processors and (b) circuitry, configured to function as a plurality of units comprising:
(1) a first acquisition unit configured to acquire tomographic data representing information on a cross section of a fundus, which is acquired based on measurement light controlled to scan the fundus;
(2) a second acquisition unit configured to acquire a correction coefficient by performing an arithmetic operation on (a) a first approximate parameter, which is obtained by transforming, in a first dimension, a parameter of the tomographic data, and (b) a second approximate parameter, which is obtained by transforming the parameter of the tomographic data in a second dimension smaller than the first dimension;
(3) a correction unit configured to correct the tomographic data using the correction coefficient; and
(4) a generation unit configured to generate an image using the corrected tomographic data.

11. An information processing apparatus according to claim 10, wherein the parameter includes at least one of a luminance value or a phase.

12. An information processing apparatus according to claim 1, wherein the correction unit is configured to correct a distribution of a parameter of the at least one piece of tomographic data in which the parameter has a value equal to or larger than a threshold.

13. An information processing apparatus according to claim 12, wherein the threshold is determined based on at least one piece of tomographic data among the plurality of pieces of tomographic data.

14. An information processing apparatus according to claim 13, wherein the threshold is determined based on any one of: a value of the parameter of at least one piece of tomographic data among the plurality of pieces of tomographic data; and a frequency of the parameter.

15. An information processing apparatus according to claim 12, wherein the threshold is determined for each imaging apparatus configured to image the cross section of the fundus.

16. An information processing apparatus according to claim 1, wherein the correction unit is configured to correct a distribution of a parameter of the at least one piece of tomographic data by correcting at least one of an average value, a median, a maximum value, a mode, a variance, or a frequency width in the distribution of the parameter.

17. An information processing apparatus according to claim 1, wherein the correction unit is configured to correct a distribution of a parameter of the at least one piece of tomographic data for each distribution of the parameter of a piece of tomographic data corresponding to at least one time of B-scan.

18. An information processing apparatus according to claim 1, wherein the correction unit is configured to correct a distribution of a parameter of the at least one piece of tomographic data for each distribution of the parameter of a piece of tomographic data corresponding to at least one time of A-scan.

19. An information processing apparatus according to claim 1, wherein the correction unit is configured to correct a distribution of a parameter of a piece of tomographic data corresponding to a retina part of the fundus.

20. An information processing apparatus according to claim 1, wherein the correction unit is configured to correct a distribution of a parameter of a piece of tomographic data for which a statistical value of a value of the parameter is smaller than a predetermined threshold among the plurality of pieces of tomographic data.

21. An information processing apparatus according to claim 1, wherein the correction unit is configured to:
compare a distribution of a parameter of the at least one piece of the tomographic data with a distribution of a parameter of at least one piece of tomographic data among the plurality of pieces of tomographic data; and
correct a distribution of the parameter of a piece of tomographic data for which a difference in statistical value between distributions to be compared is larger than a predetermined threshold.

22. An information processing apparatus according to claim 20, wherein the statistical value includes at least one of a sum, an average value, a median, a maximum value, a variance, or a mode.

23. An information processing method comprising:
acquiring a plurality of pieces of tomographic data each representing information on a cross section of a fundus, which is acquired based on measurement light controlled to scan the same position of the fundus;
acquiring a correction coefficient by performing an arithmetic operation on (a) a first approximate parameter, which is obtained by transforming, in a first dimension, a parameter of a piece of tomographic data to be used for calculating a motion contrast, and (b) a second approximate parameter, which is obtained by transforming the parameter of the piece of tomographic data in a second dimension smaller than the first dimension;
correcting at least one piece of tomographic data among the plurality of pieces of tomographic data using the correction coefficient; and
generating a motion contrast image based on a motion contrast calculated using the plurality of pieces of tomographic data including the corrected at least one piece of tomographic data.

24. An information processing method comprising:
acquiring a plurality of pieces of tomographic data each representing information on a cross section of a fundus, which is acquired based on measurement light controlled to scan the same position of the fundus;
acquiring a correction coefficient by performing an arithmetic operation on (a) a first approximate parameter, which is obtained by transforming, in a first dimension, a parameter of a piece of tomographic data to be used for calculating a motion contrast, and (b) a second approximate parameter, which is obtained by transforming the parameter of the piece of tomographic data in a second dimension smaller than the first dimension;
correcting a threshold of threshold processing to be applied to the parameter of the plurality of pieces of tomographic data using the correction coefficient; and
generating a motion contrast image based on a motion contrast calculated using a parameter of at least one piece of tomographic data among the plurality of pieces of tomographic data, which has been subjected to the threshold processing using the corrected threshold.

25. An information processing method comprising:
acquiring tomographic data representing information on a cross section of a fundus, which is acquired based on measurement light controlled to scan the fundus;
acquiring a correction coefficient by performing an arithmetic operation on (a) a first approximate parameter, which is obtained by transforming, in a first dimension, a parameter of the tomographic data, and (b) a second approximate parameter, which is obtained by transforming the parameter of the tomographic data in a second dimension smaller than the first dimension;
correcting the tomographic data using the correction coefficient; and
generating an image using the corrected tomographic data.

26. A non-transitory computer-readable medium having stored thereon a program for causing a processor to execute each step of the information processing method according to claim 23 when executed by the processor.

27. A non-transitory computer-readable medium having stored thereon a program for causing a processor to execute each step of the information processing method according to claim 24 when executed by the processor.

28. A non-transitory computer-readable medium having stored thereon a program for causing a processor to execute steps of the information processing method according to claim 25 when executed by the processor.

29. An information processing apparatus according to claim 10, wherein the second acquisition unit is configured to:
calculate the first approximate parameter by transforming, in a two-dimensional direction, the parameter of the tomographic data corresponding to a front of the fundus; and
calculate the second approximate parameter by transforming, in a one-dimensional direction, the parameter of the tomographic data corresponding to the front of the fundus.

30. An information processing apparatus according to claim 29, wherein the one-dimensional direction includes an axial direction of main scanning by the measurement light.

31. An information processing apparatus according to claim 10, wherein the arithmetic operation includes an operation of dividing the first approximate parameter by the second approximate parameter.

32. An information processing apparatus according to claim 10, wherein the transformation includes one of smoothing and performing morphology calculation.

33. An information processing apparatus according to claim 10, wherein the first approximate parameter is acquired by transforming, in a two-dimensional direction, a projection image of a front of the fundus obtained by using a three-dimensional volume data including the tomographic data, and wherein the second approximate parameter is acquired by transforming, in a one-dimensional direction, the projection image.

34. An information processing apparatus according to claim 1, wherein the first approximate parameter is acquired by transforming, in a two-dimensional direction, a projection image of a front of the fundus obtained by using a three-dimensional volume data including the tomographic data, and wherein the second approximate parameter is acquired by transforming, in a one-dimensional direction, the projection image.

35. An information processing apparatus comprising:
at least one of (a) one or more processors and (b) circuitry, configured to function as a plurality of units comprising:
(1) a first acquisition unit configured to acquire a plurality of pieces of tomographic data each representing information on a cross section of a fundus, which is acquired based on measurement light controlled to scan the same position of the fundus;
(2) a second acquisition unit configured to acquire a correction coefficient by performing an arithmetic operation on (a) a first approximate parameter, which is obtained by transforming, in a first dimension, a parameter relating to a motion contrast, and (b) a second approximate parameter, which is obtained by transforming the parameter in a second dimension smaller than the first dimension;
(3) a correction unit configured to correct data relating to the motion contrast using the correction coefficient; and
(4) a generation unit configured to generate an image using the corrected data relating to the motion contrast.

36. An information processing method comprising:
acquiring a plurality of pieces of tomographic data each representing information on a cross section of a fundus, which is acquired based on measurement light controlled to scan the same position of the fundus;
acquiring a correction coefficient by performing an arithmetic operation on (a) a first approximate parameter, which is obtained by transforming, in a first dimension, a parameter relating to a motion contrast, and (b) a second approximate parameter, which is obtained by transforming the parameter in a second dimension smaller than the first dimension;
correcting data relating to the motion contrast using the correction coefficient; and
generating an image using the corrected data relating to the motion contrast.

37. A non-transitory computer-readable medium having stored thereon a program for causing a processor to execute each step of the information processing method according to claim 36 when executed by the processor.

* * * * *